United States Patent
Kojima et al.

(10) Patent No.: US 11,197,653 B2
(45) Date of Patent: Dec. 14, 2021

(54) TOMOSYNTHESIS IMAGING APPARATUS, METHOD FOR OPERATING TOMOSYNTHESIS IMAGING APPARATUS, AND PROGRAM FOR OPERATING TOMOSYNTHESIS IMAGING APPARATUS

(71) Applicant: FUJIFILM CORPORATION, Tokyo (JP)

(72) Inventors: Tetsuya Kojima, Kanagawa (JP); Masayoshi Matsuura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 30 days.

(21) Appl. No.: 16/776,519

(22) Filed: Jan. 30, 2020

(65) Prior Publication Data

US 2020/0261044 A1    Aug. 20, 2020

(30) Foreign Application Priority Data

Feb. 14, 2019   (JP) .............................. JP2019-024849

(51) Int. Cl.
    *A61B 6/00*   (2006.01)
    *A61B 6/02*   (2006.01)

(52) U.S. Cl.
    CPC .............. *A61B 6/502* (2013.01); *A61B 6/025* (2013.01); *A61B 6/4007* (2013.01); *A61B 6/582* (2013.01)

(58) Field of Classification Search
    CPC .......... A61B 6/502; A61B 6/025; A61B 6/582
    See application file for complete search history.

(56) References Cited

U.S. PATENT DOCUMENTS

| | | | |
|---|---|---|---|
| 2012/0219110 A1* | 8/2012 | Albanese | A61B 6/502 378/37 |
| 2015/0030119 A1 | 1/2015 | Tamura et al. | |
| 2016/0206264 A1* | 7/2016 | Fukuda | A61B 6/545 |

FOREIGN PATENT DOCUMENTS

| | | |
|---|---|---|
| DE | 102010011663 A1 | 9/2011 |
| JP | 2010-119507 A | 6/2010 |

OTHER PUBLICATIONS

Extended European Search Report dated Jul. 14, 2020, issued in corresponding EP Patent Application No. 20155970.5.

* cited by examiner

*Primary Examiner* — Chih-Cheng Kao
(74) *Attorney, Agent, or Firm* — Solaris Intellectual Property Group, PLLC

(57) ABSTRACT

A mammography apparatus includes a radiation source having a plurality of radiation tubes. The plurality of radiation tubes are disposed at a plurality of positions where the radiation is emitted to an imaging surface of a radiation detector at different irradiation angles. A correction unit corrects irradiation conditions of the radiation using a first coefficient such that the arrival dose of the radiation reaching the radiation detector is the same regardless of the irradiation angle. The first coefficient corresponds to a compression thickness of the object, indicates a rate of change in an arrival dose of the radiation depending on the irradiation angle, and is registered for each of the plurality of radiation tubes. The setting unit sets the irradiation conditions corrected by the correction unit in the radiation source.

10 Claims, 29 Drawing Sheets

FIG. 11

Table 60: FIRST COEFFICIENT Kfp (i,Thj)

| RADIATION TUBE | Th1 | Th2 | Th3 | ... |
|---|---|---|---|---|
| 1(SP1) | 1.22 | 1.23 | 1.24 | ... |
| 2(SP2) | 1.2 | 1.21 | 1.22 | ... |
| ⋮ | ⋮ | | | |
| 8(SP8) | 1 | 1 | 1 | ... |
| ⋮ | ⋮ | | | |
| 14(SP14) | 1.2 | 1.21 | 1.22 | ... |
| 15(SP15) | 1.22 | 1.23 | 1.24 | ... |

FIG. 12

Table 61

| RADIATION TUBE | SECOND COEFFICIENT Kmd (i) |
|---|---|
| 1(SP1) | 1.05 |
| 2(SP2) | 1.2 |
| ⋮ | ⋮ |
| 8(SP8) | 1.12 |
| ⋮ | ⋮ |
| 14(SP14) | 0.86 |
| 15(SP15) | 0.94 |

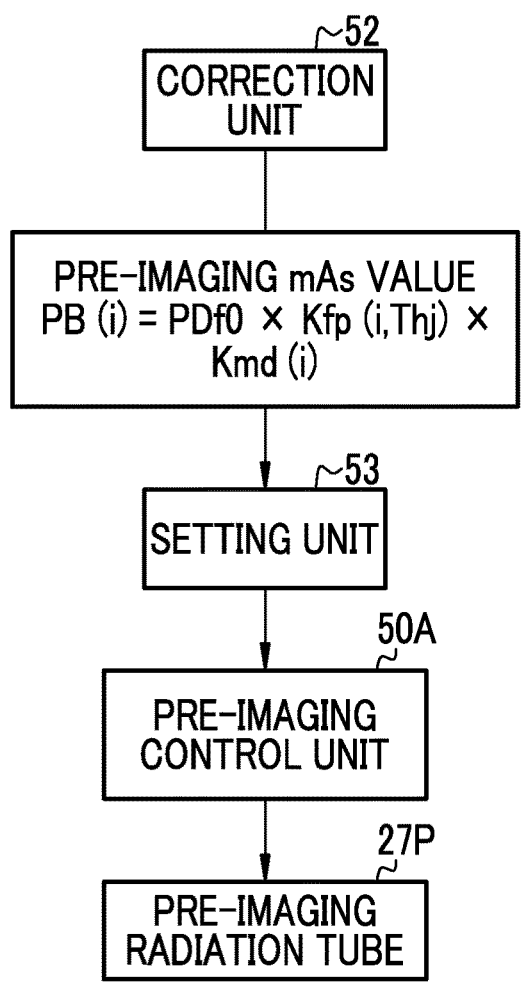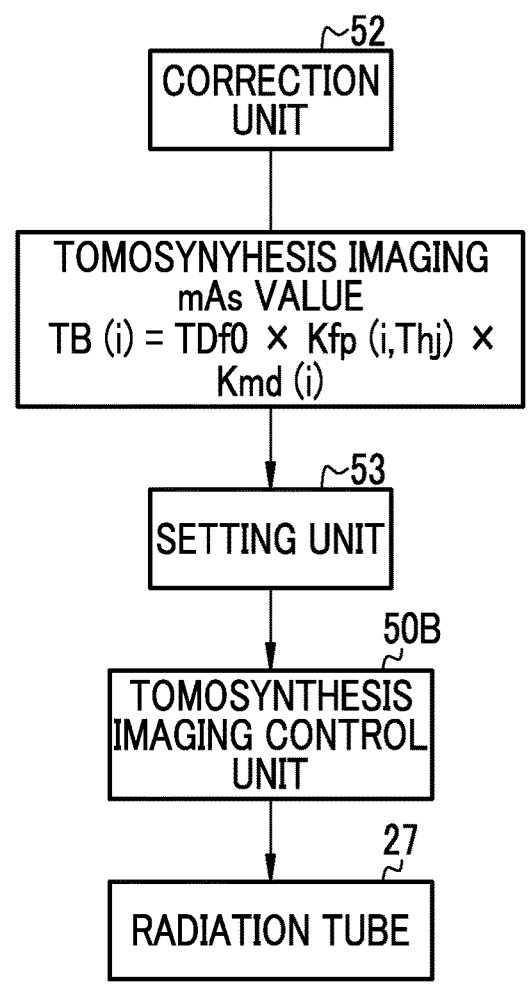

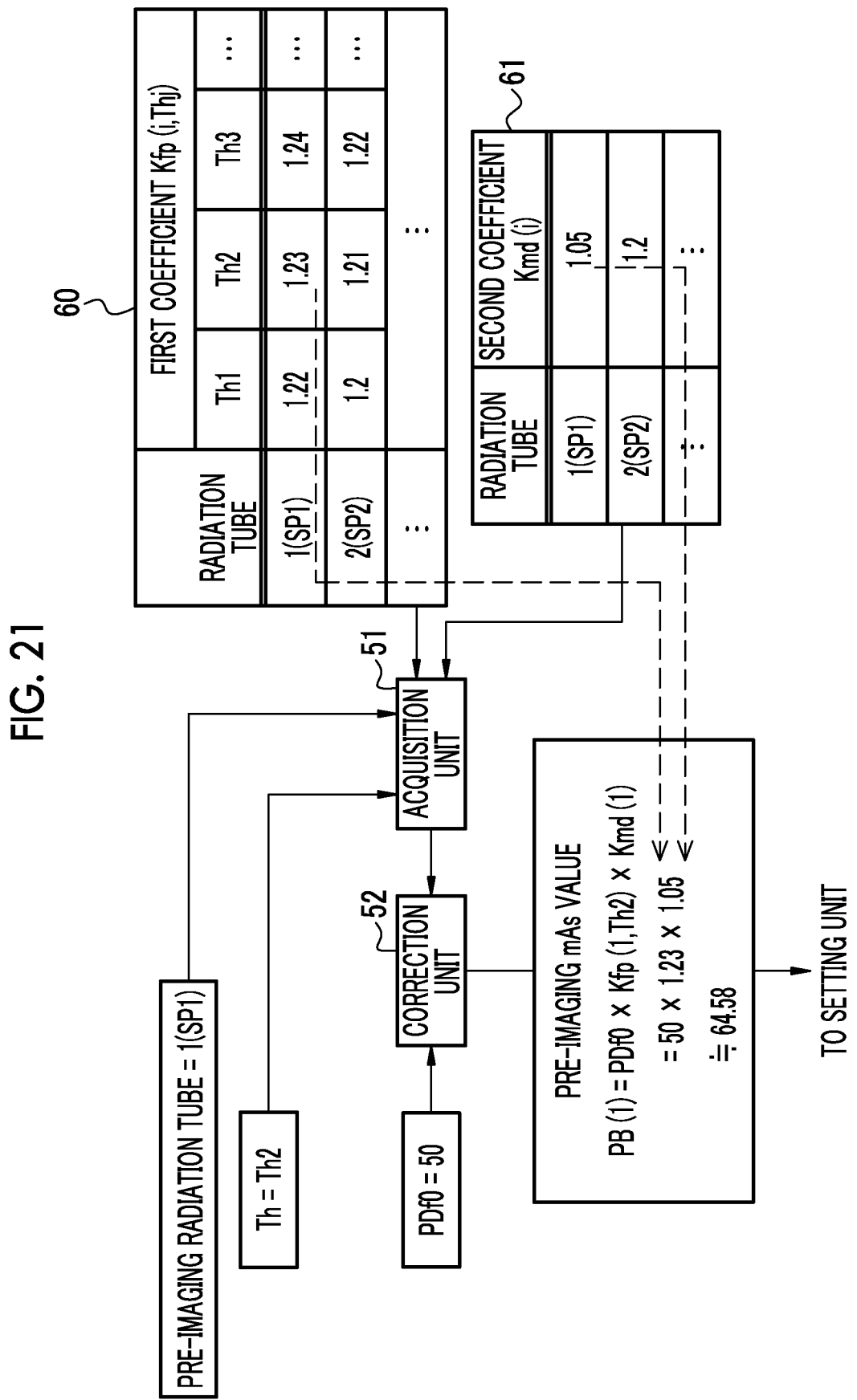

FIG. 25

| RADIATION TUBE | IRRADIATION CONDITION | OUTPUT VALUE |
|---|---|---|
| 1(SP1) | TDf0 | 82 |
| 2(SP2) | TDf0 | 83 |
| ⋮ | ⋮ | ⋮ |
| 8(SP8) | TDf0 | 100 |
| ⋮ | ⋮ | ⋮ |
| 14(SP14) | TDf0 | 83 |
| 15(SP15) | TDf0 | 82 |

CORRECT BY USING FIRST COEFFICIENT AND SECOND COEFFICIENT

| RADIATION TUBE | IRRADIATION CONDITION | OUTPUT VALUE |
|---|---|---|
| 1(SP1) | TB(1) | 100 |
| 2(SP2) | TB(2) | 100 |
| ⋮ | ⋮ | ⋮ |
| 8(SP8) | TB(8) | 100 |
| ⋮ | ⋮ | ⋮ |
| 14(SP14) | TB(14) | 100 |
| 15(SP15) | TB(15) | 100 |

FIG. 31

| RADIATION TUBE | MEASURED INITIAL OUTPUT VALUE | MEASURED PASSAGE OUTPUT VALUE | RATE OF REDUCTION |
|---|---|---|---|
| 1(SP1) | 500 | 450 | 0.9(=450/500) |
| 2(SP2) | 570 | 520 | 0.91(≒520/570) |
| ... | ... | ... | ... |
| 8(SP3) | 530 | 430 | 0.81(≒430/530) |
| ... | ... | ... | ... |
| 14(SP14) | 410 | 360 | 0.88(≒360/410) |
| 15(SP15) | 450 | 390 | 0.87(≒390/450) |

FIG. 32

| RADIATION TUBE | SECOND COEFFICIENT Kmd (i) |
|---|---|
| 1(SP1) | 1.05 |
| 2(SP2) | 1.2 |
| ... | ... |
| 8(SP3) | 1.12 |
| ... | ... |
| 14(SP14) | 0.86 |
| 15(SP15) | 0.94 |

61

CALIBRATION UNIT

| RATE OF REDUCTION |
|---|
| 0.9 |
| 0.91 |
| ... |
| 0.81 |
| ... |
| 0.88 |
| 0.87 |

100

| RADIATION TUBE | SECOND COEFFICIENT Kmd (i) |
|---|---|
| 1(SP1) | 1.17 (≒1.05/0.9) |
| 2(SP2) | 1.32 (≒1.2/0.91) |
| ... | ... |
| 8(SP3) | 1.38 (≒1.12/0.81) |
| ... | ... |
| 14(SP14) | 0.98 (≒0.86/0.88) |
| 15(SP15) | 1.08 (≒0.94/0.87) |

101

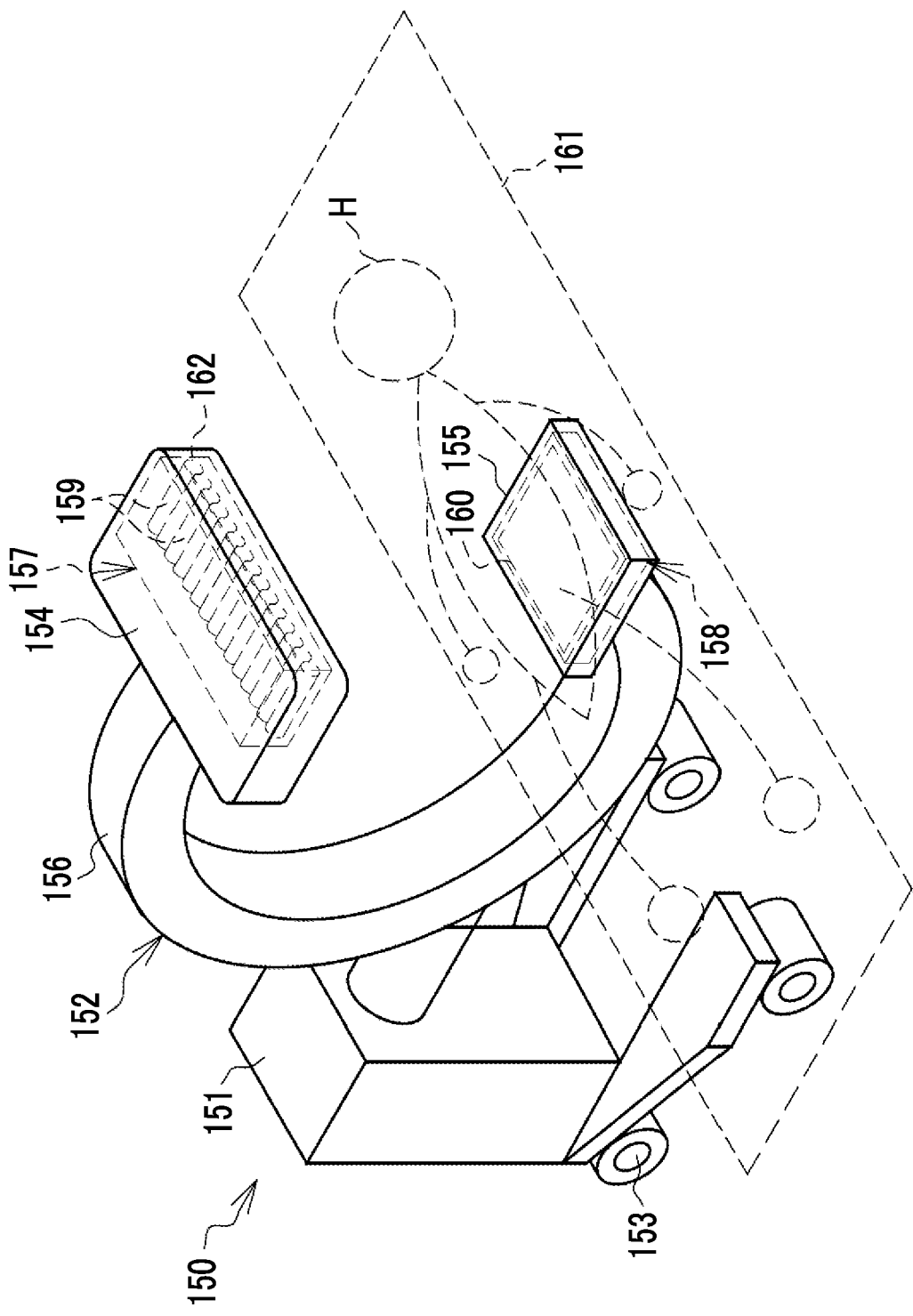

TOMOSYNTHESIS IMAGING APPARATUS, METHOD FOR OPERATING TOMOSYNTHESIS IMAGING APPARATUS, AND PROGRAM FOR OPERATING TOMOSYNTHESIS IMAGING APPARATUS

CROSS-REFERENCE TO RELATED APPLICATIONS

The present application claims priority under 35 U.S.C. § 119 to Japanese Patent Application No. 2019-024849, filed on Feb. 14, 2019. The above application is hereby expressly incorporated by reference, in its entirety, into the present application.

BACKGROUND

1. Technical Field

The technology according to the present disclosure relates to a tomosynthesis imaging apparatus, a method for operating the tomosynthesis imaging apparatus, and a program for operating the tomosynthesis imaging apparatus.

2. Description of the Related Art

A tomosynthesis imaging apparatus has been known which performs tomosynthesis imaging that moves a radiation tube to a plurality of positions with respect to a radiation detector and emits radiation from the radiation tube at each position. The focuses of the radiation at the plurality of positions to which the radiation tube is moved are arranged, for example, in a linear shape or an arc shape at equal intervals. In the tomosynthesis imaging, the radiation is emitted to an imaging surface of the radiation detector at a plurality of irradiation angles and a plurality of projection images of an object irradiated with the radiation at different irradiation angles are captured. Then, tomographic images in any tomographic planes of the object are generated on the basis of the plurality of projection images.

JP2010-119507A discloses a tomosynthesis imaging apparatus that comprises a plurality of radiation tubes, instead of one radiation tube, in order to reduce the imaging time. The tomosynthesis imaging apparatus disclosed in JP2010-119507A corrects the irradiation conditions of the plurality of radiation tubes, using a coefficient related to a tube current-irradiation time product (also referred to as a mAs value) which has been stored in advance, such that the doses of the radiation emitted from the plurality of radiation tubes are equal to each other.

SUMMARY

For example, in a case in which an image of an object which is flat in the lateral direction, such as the breast compressed by a compression plate, is captured, the transmission distance of radiation through the object becomes longer as the irradiation angle becomes larger. That is, as the irradiation angle becomes larger, the amount of radiation absorbed by the object becomes larger. Therefore, under the same irradiation conditions, the arrival dose of radiation reaching the radiation detector becomes lower as the irradiation angle becomes larger. As a result, in a case in which a plurality of radiation tubes are provided, the arrival doses of the radiation reaching the radiation detector from each radiation tube are different from each other.

An object of the technology according to the present disclosure is to provide a tomosynthesis imaging apparatus that can perform correction such that an arrival dose of radiation is the same regardless of an irradiation angle in a case in which the radiation is emitted from a plurality of radiation tubes at different irradiation angles, a method for operating the tomosynthesis imaging apparatus, and a program for operating the tomosynthesis imaging apparatus.

In order to achieve the object, according to the present disclosure, there is provided a tomosynthesis imaging apparatus comprising: a radiation detector that detects radiation transmitted through an object and has an imaging surface capturing a projection image of the object; a radiation source having a plurality of radiation tubes disposed at a plurality of positions where the radiation is emitted to the imaging surface at different irradiation angles; an acquisition unit that acquires a first coefficient which corresponds to a thickness of the object, indicates a rate of change in an arrival dose of the radiation reaching the radiation detector depending on the irradiation angle, and is registered for each of the plurality of radiation tubes; a correction unit that corrects irradiation conditions of the radiation using the first coefficient; and a setting unit that sets the irradiation conditions corrected by the correction unit in the radiation source.

Preferably, the first coefficient is a value obtained by dividing a measured reference output value which has been actually output by the radiation detector receiving the radiation emitted from a radiation tube of which the irradiation angle is disposed at a reference position by a measured target output value which has been actually output by the radiation detector receiving the radiation emitted from a radiation tube of which the first coefficient is to be calculated.

Preferably, the first coefficient is a value obtained by dividing a theoretical reference output value that is theoretically estimated to be output from the radiation detector receiving the radiation emitted from a radiation tube of which the irradiation angle is disposed at a reference position by a theoretical target output value that is theoretically estimated to be output from the radiation detector receiving the radiation emitted from a radiation tube of which the first coefficient is to be calculated.

Preferably, the acquisition unit acquires a second coefficient that is related to a dose of the radiation and is registered for each of the plurality of radiation tubes, and the correction unit corrects the irradiation conditions using the second coefficient in addition to the first coefficient.

Preferably, the tomosynthesis imaging apparatus further comprises a calibration unit that calibrates the second coefficient using a rate of reduction in the radiation dose caused by deterioration of the radiation tube over time.

Preferably, the second coefficient is a tube current-irradiation time product per unit dose.

Preferably, the correction unit corrects the tube current-irradiation time product included in the irradiation conditions.

Preferably, at the plurality of positions, focuses of the radiation are arranged in a linear shape or an arc shape at equal intervals.

Preferably, the tomosynthesis imaging apparatus is a mammography apparatus that uses a breast as the object.

According to the present disclosure, there is provided a method for operating a tomosynthesis imaging apparatus comprising a radiation detector that detects radiation transmitted through an object and has an imaging surface capturing a projection image of the object. The method comprises: an acquisition step of acquiring, using a radiation source having a plurality of radiation tubes disposed at a plurality of positions where the radiation is emitted to the imaging surface at different irradiation angles, a first coefficient which corresponds to a thickness of the object, indicates a rate of change in an arrival dose of the radiation reaching the radiation detector depending on the irradiation angle, and is registered for each of the plurality of radiation tubes; a correction step of correcting irradiation conditions of the radiation using the first coefficient; and a setting step of setting the irradiation conditions corrected in the correction step in the radiation source.

According to the present disclosure, there is provided a program for operating a tomosynthesis imaging apparatus comprising a radiation detector that detects radiation transmitted through an object and has an imaging surface capturing a projection image of the object and a radiation source having a plurality of radiation tubes disposed at a plurality of positions where the radiation is emitted to the imaging surface at different irradiation angles. The program causes a computer to function as: an acquisition unit that acquires a first coefficient which corresponds to a thickness of the object, indicates a rate of change in an arrival dose of the radiation reaching the radiation detector depending on the irradiation angle, and is registered for each of the plurality of radiation tubes; a correction unit that corrects irradiation conditions of the radiation using the first coefficient; and a setting unit that sets the irradiation conditions corrected by the correction unit in the radiation source.

According to the technology of the present disclosure, it is possible to provide a tomosynthesis imaging apparatus that can perform correction such that an arrival dose of radiation is the same regardless of an irradiation angle in a case in which the radiation is emitted from a plurality of radiation tubes at different irradiation angles, a method for operating the tomosynthesis imaging apparatus, and a program for operating the tomosynthesis imaging apparatus.

BRIEF DESCRIPTION OF THE DRAWINGS

Exemplary embodiments according to the technique of the present disclosure will be described in detail based on the following figures, wherein:

FIG. 11 is a diagram illustrating a first coefficient table;

FIG. 12 is a diagram illustrating a second coefficient table;

FIGS. 20A and 20B are diagrams illustrating the outline of a process of a correction unit; FIG. 20A illustrates an aspect in which irradiation conditions are corrected in pre-imaging and FIG. 20B illustrates an aspect in which irradiation conditions are corrected in tomosynthesis imaging;

FIG. 21 is a diagram illustrating an aspect in which the correction unit calculates a pre-imaging mAs value;

FIG. 25 is a diagram illustrating the effect of correcting the irradiation conditions using the first coefficient and the second coefficient;

FIG. 31 is a diagram illustrating an aspect in which a rate of reduction in the dose of radiation from each radiation tube is calculated;

FIG. 32 is a diagram illustrating an aspect in which the second coefficient is calibrated using the rate of reduction;

FIG. 34 is a diagram illustrating an imaging apparatus for surgery.

DETAILED DESCRIPTION

First Embodiment

Figure 1:
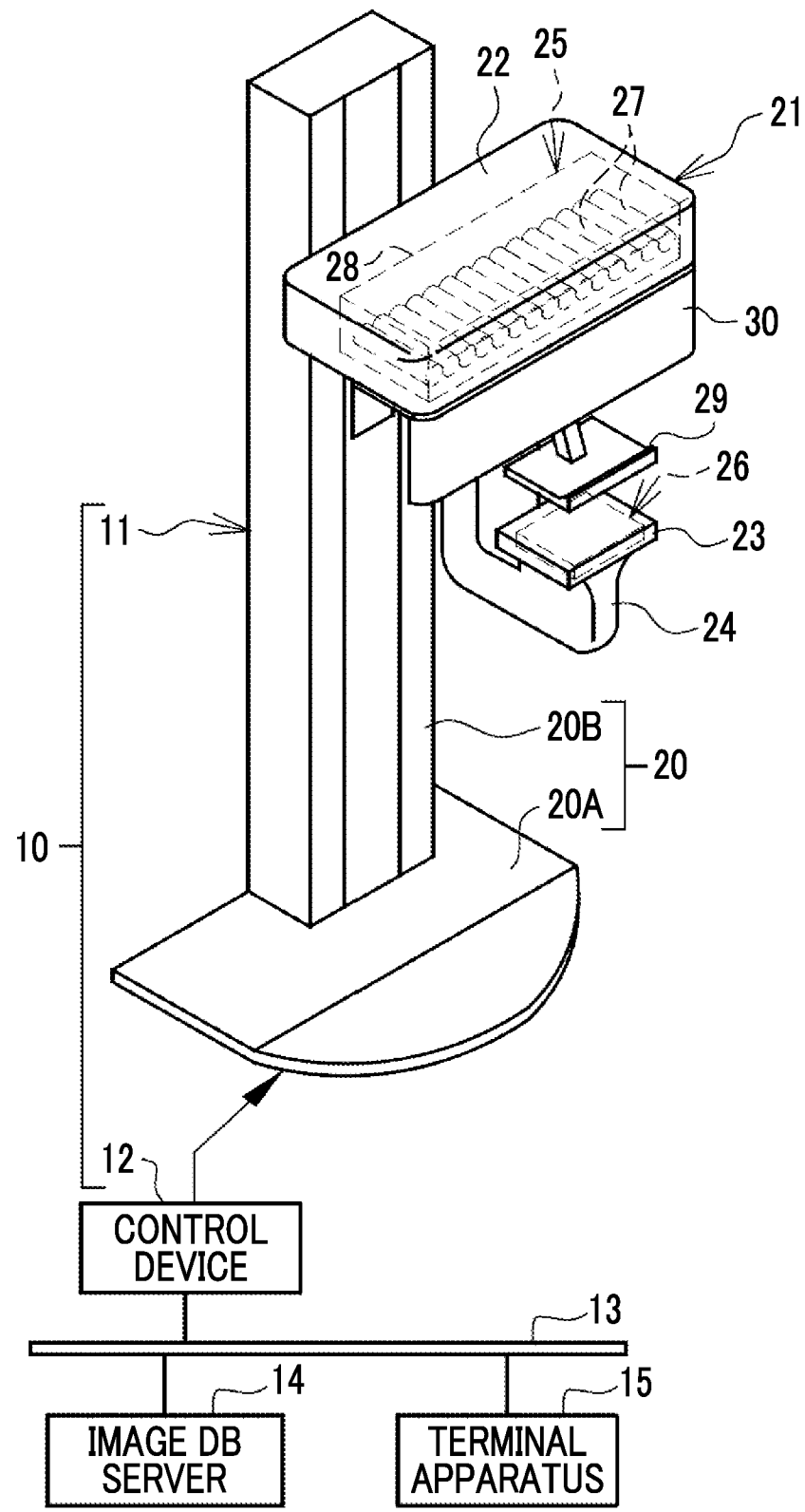
FIG. 1 is a diagram illustrating, for example, a mammography apparatus.
Figure 2:
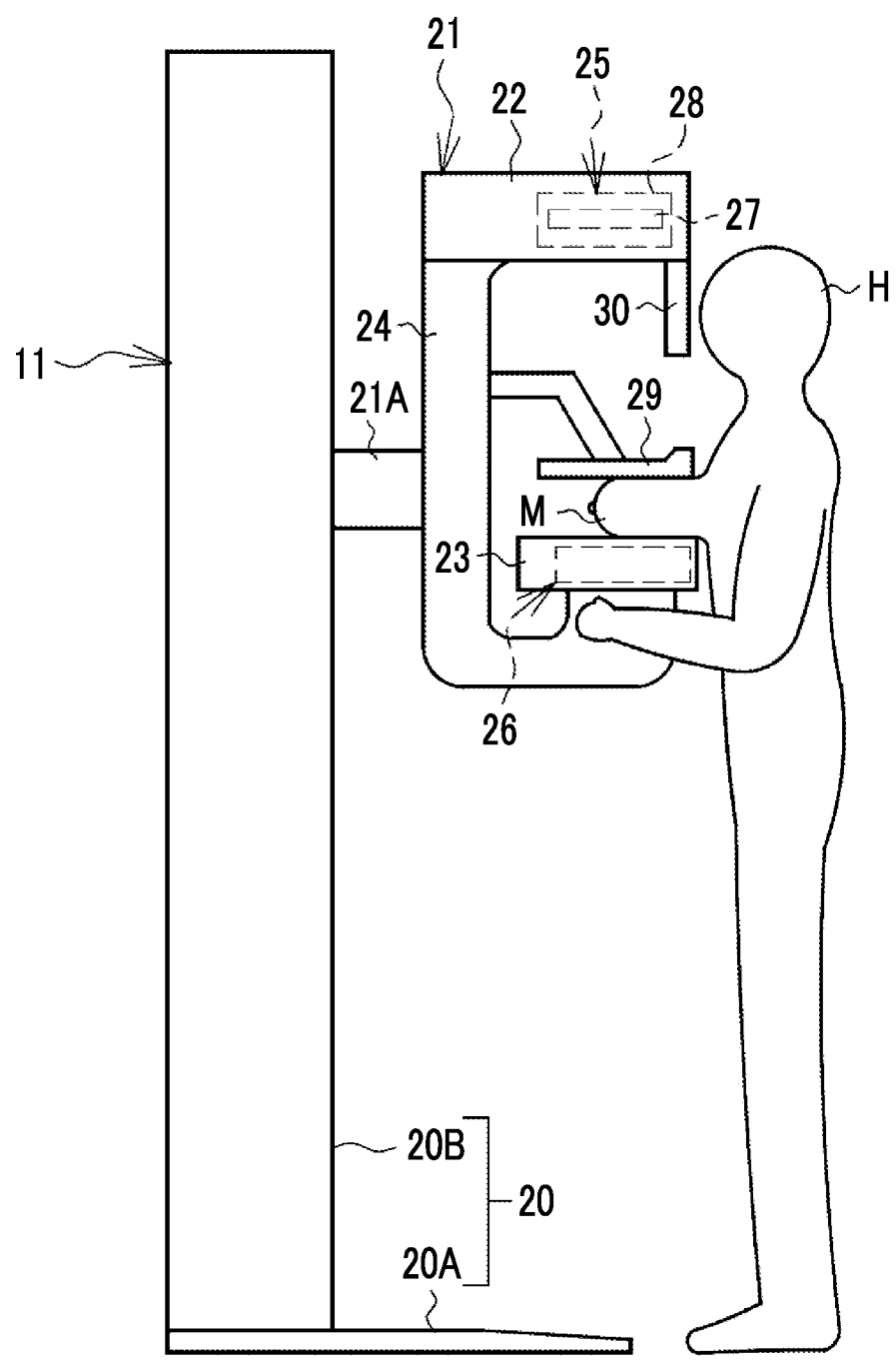
FIG. 2 is a diagram illustrating an apparatus main body of a mammography apparatus.

In FIGS. 1 and 2, a mammography apparatus 10 which is an example of a "tomosynthesis imaging apparatus" according to the technology of the present disclosure uses a breast M of a subject H as an object. The mammography apparatus 10 irradiates the breast M with radiation 37 (see, for example, FIG. 4), such as X-rays or γ-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is connected to an image database (hereinafter, referred to as DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, and accumulates and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of radiation tubes 27, for example, 15 radiation tubes 27 and a housing 28 that accommodates the radiation tubes 27. The radiation tubes 27 are used for tomosynthesis imaging which captures a plurality of projection images of the breast M at different irradiation angles as radiographic images. One of the radiation tubes 27 is used for pre-imaging which is performed before the tomosynthesis imaging in order to set the irradiation conditions of the radiation 37 in the tomosynthesis imaging. The radiation detector 26 detects the radiation 37 transmitted through the breast M and outputs a radiographic image. The number of radiation tubes 27 is not limited to 15 in the above-mentioned example.

A compression plate 29 is attached between the radiation source accommodation portion 22 and the detector accommodation portion 23 in the main body portion 24. The compression plate 29 is made of a material that transmits the radiation 37. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
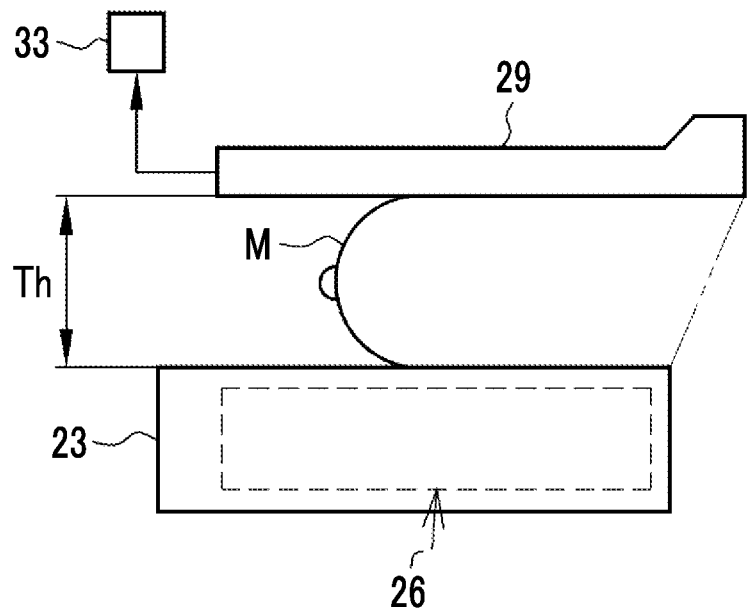
FIG. 3 is a diagram illustrating an aspect in which a compression thickness of the breast is measured.

In FIG. 3, a measurement sensor 33 that measures a compression thickness Th of the breast M is connected to the compression plate 29. The measurement sensor 33 is, for example, a linear potentiometer that is provided in the support 20B and measures the height of the compression plate 29 from the detector accommodation portion 23 as the compression thickness Th. The measurement sensor 33 measures the compression thickness Th at an interval of, for example, 1 mm. The compression thickness Th is an example of "the thickness of an object" according to the technology of the present disclosure.

Figure 4:
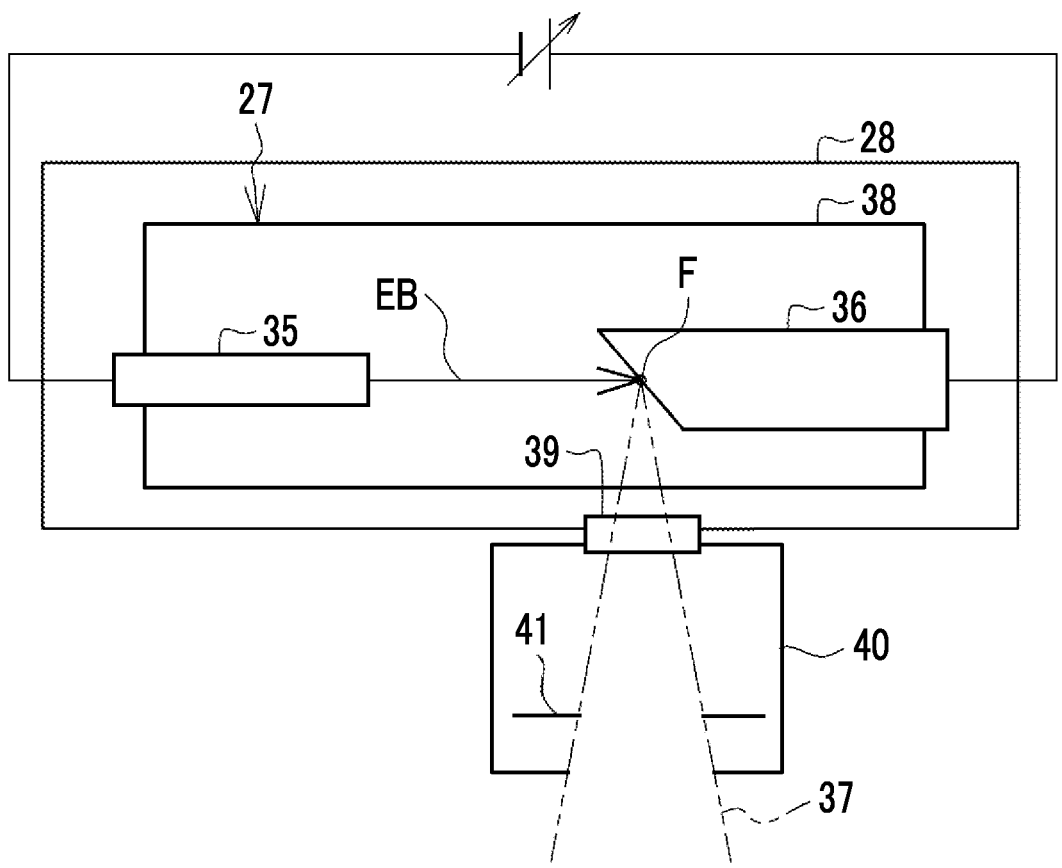
FIG. 4 is a diagram illustrating a radiation tube.

In FIG. 4, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38. The cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

The housing 28 is provided with a radiation transmission window 39 that transmits the radiation 37. The radiation 37 emitted from the anode 36 is emitted to the outside of the housing 28 through the radiation transmission window 39. In addition, the housing 28 is filled with insulating oil.

An irradiation field limiter 40 (not illustrated in FIGS. 1 and 2) is provided below the radiation transmission window 39 in the height direction. The irradiation field limiter 40 is also called a collimator and sets the irradiation field of the radiation 37 in an imaging surface 45 (see FIG. 5) of the radiation detector 26. Specifically, the irradiation field limiter 40 includes a plurality of shielding plates 41 which are made of, for example, lead and shield the radiation 37 transmitted through the radiation transmission window 39. The shielding plates 41 are moved to change the size of, for example, a rectangular irradiation opening defined by the shielding plates 41, thereby setting the irradiation field of the radiation 37.

Figure 5:
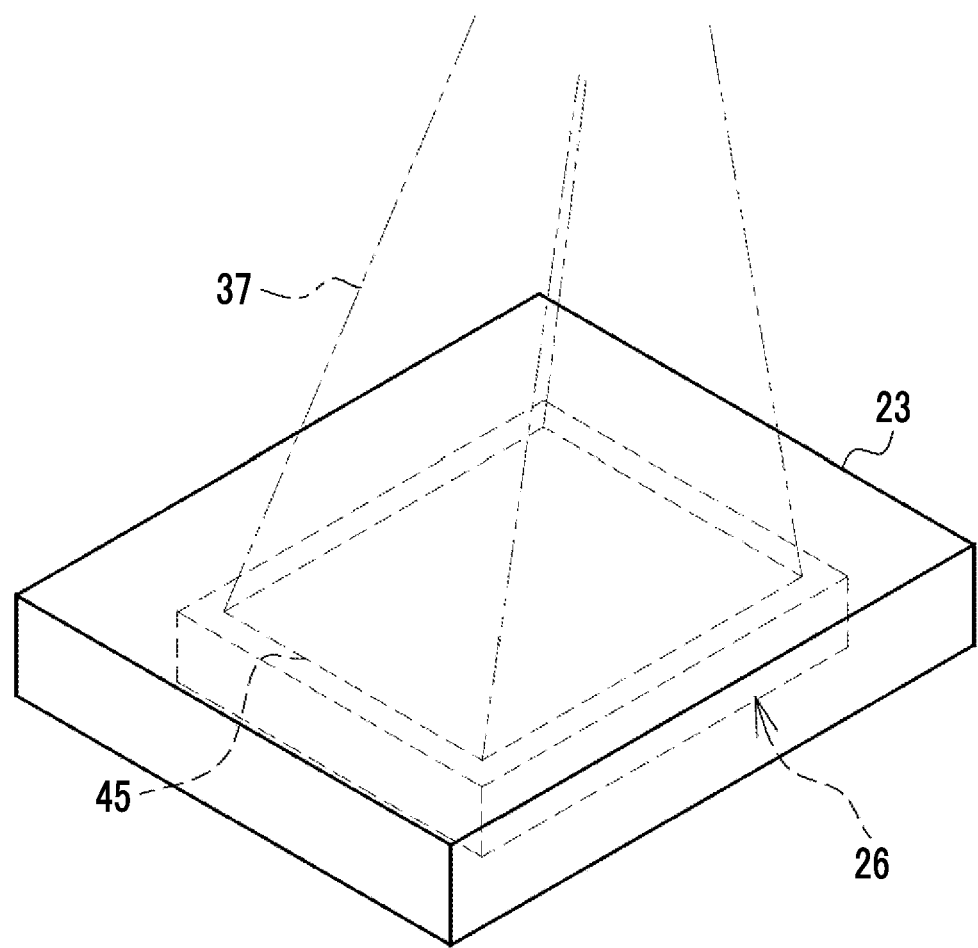
FIG. 5 is a diagram illustrating a detector accommodation portion.

In FIG. 5 illustrating the detector accommodation portion 23, the radiation detector 26 has the imaging surface 45. The imaging surface 45 detects the radiation 37 transmitted through the breast M and captures a projection image of the breast M. Specifically, the imaging surface 45 is a two-dimensional plane in which pixels converting the radiation 37 into an electric signal are two-dimensionally arranged.

The radiation detector 26 is also referred to as a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal. In the following description, the electric signal which corresponds to the radiation 37 and is output from the pixels of the imaging surface 45 may be referred to as an output value.

Figure 6:
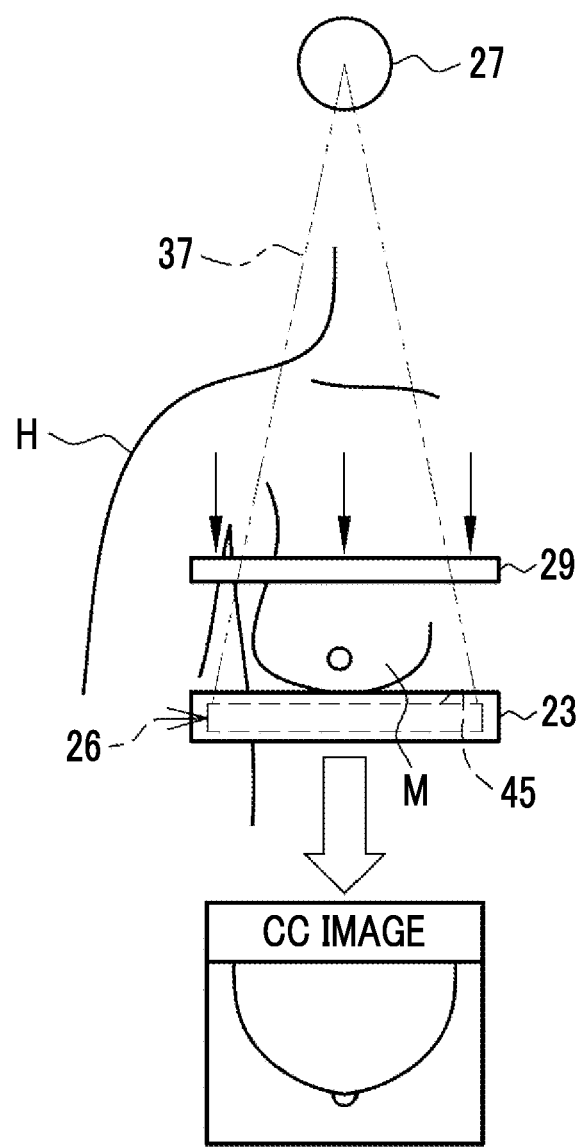
FIG. 6 is a diagram illustrating an aspect of CC imaging.
Figure 7:
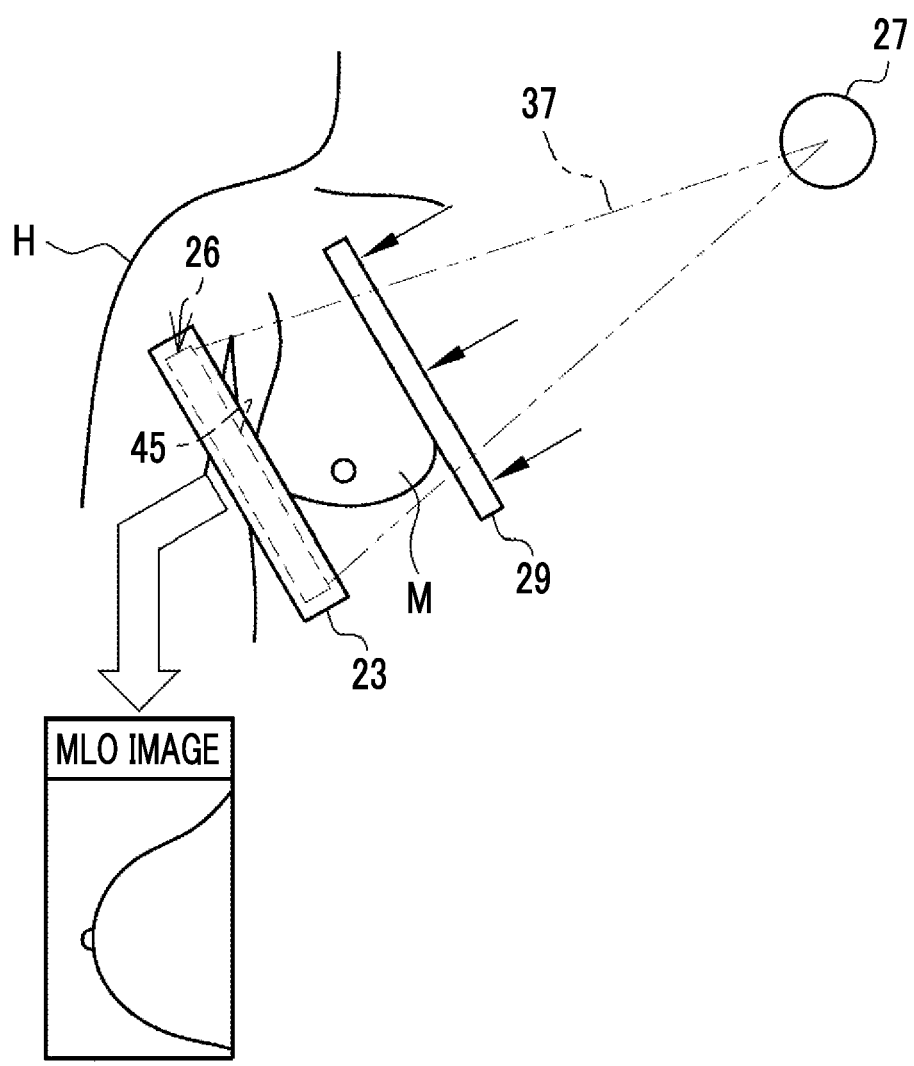
FIG. 7 is a diagram illustrating an aspect of MLO imaging.

FIGS. 6 and 7 illustrate a method for capturing an image of the breast M in the mammography apparatus 10. FIG. 6 illustrates craniocaudal view (CC) imaging and FIG. 7 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image. In addition, FIGS. 6 and 7 illustrate only one radiation tube 27 for simplicity of illustration. Further, FIGS. 6 and 7 illustrate the right breast M. Of course, the image of the left breast M may be captured.

Figure 8:
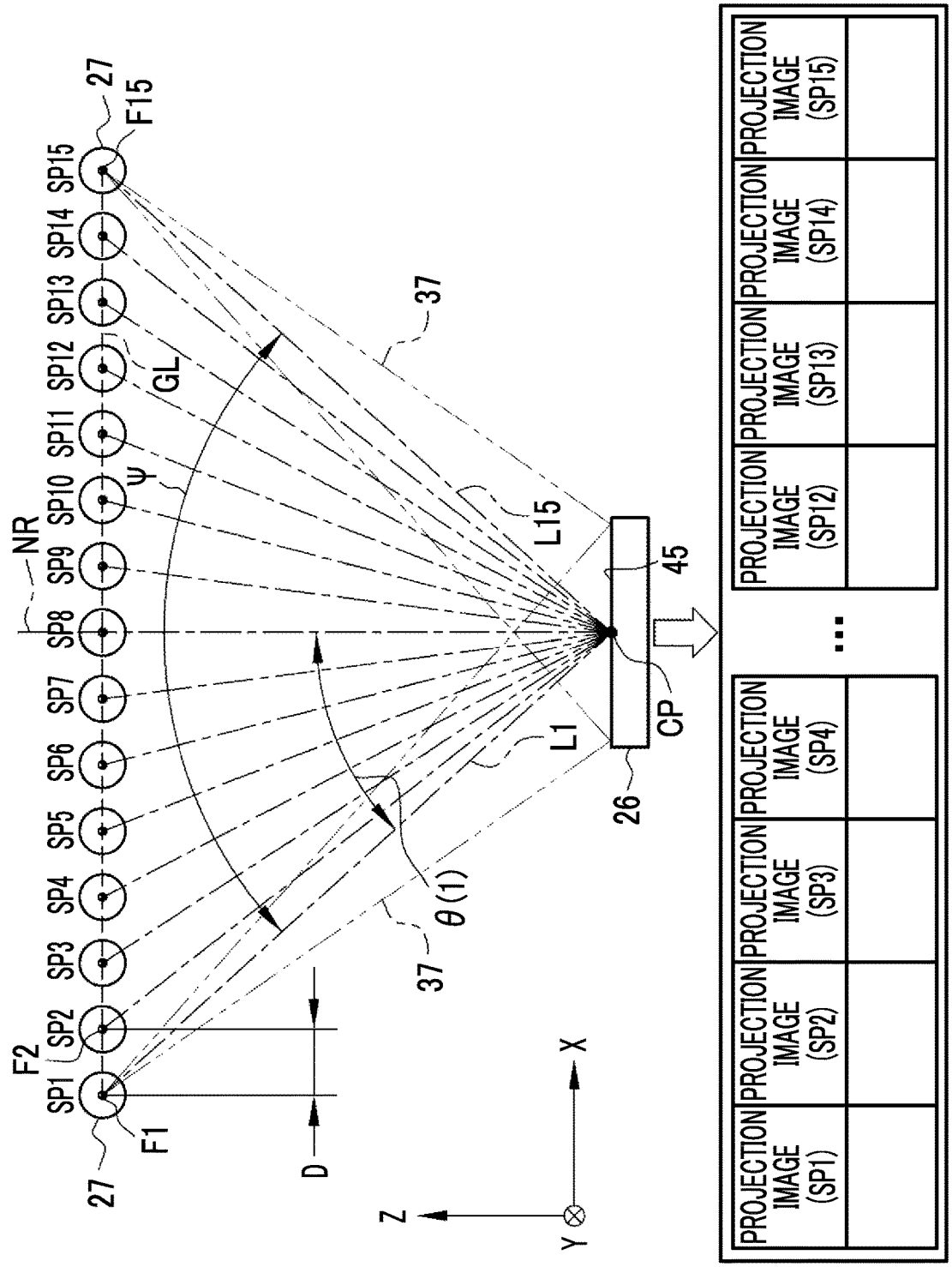
FIG. 8 is a diagram illustrating an aspect of tomosynthesis imaging.

In FIG. 8 which is a plan view illustrating the radiation source 25 and the radiation detector 26 as viewed from the support 20B, it is assumed that the direction of a normal line to the imaging surface 45 is the Z direction, a direction along a side of the imaging surface 45 is the X direction, and a depth direction of the imaging surface 45 which is perpendicular to the Z direction and the X direction is the Y direction. The radiation tubes 27 are provided at a total of 15 positions SP1, SP2, . . . , SP14, and SP15 where the radiation 37 is emitted to the imaging surface 45 at different irradiation angles. The focuses F1 to F15 of the radiation 37 in the radiation tubes 27 at the positions SP1 to SP15 are linearly arranged at equal intervals D. The position SP8 is disposed on a normal line NR to the imaging surface 45 which extends from a center point CP of the side of the imaging surface 45 along the X direction. The positions other than the position SP8 are bilaterally symmetric with respect to the normal line NR such that the positions SP1 to SP7 are disposed on the left side of the normal line NR and the positions SP9 to SP15 are disposed on the right side of the normal line NR.

Here, a straight line GL on which the positions SP1 to SP15 are set is parallel to the side of the imaging surface 45 along the X direction in a plan view of the radiation source 25 and the radiation detector 26 from the Z direction. The straight line GL is offset to the front side (a side opposite to the support 20B) in the Y direction. The present disclosure is not limited to the case in which the intervals D between the focuses F1 to F15 are exactly equal to each other. For example, an error of ±5% is allowed.

The irradiation angle of the radiation 37 is an angle formed between the normal line NR and a line connecting the center point CP and each of the focuses F1 to F15 of the radiation 37 in the radiation tubes 27 at the positions SP1 to SP15. For example, FIG. 8 illustrates a line L1 connecting the focus F1 at the position SP1 and the center point CP and an irradiation angle θ(1) which is an angle formed between the normal line NR and the line L1.

An angle represented by a symbol is the maximum scanning angle of tomosynthesis imaging. The maximum scanning angle is defined by the positions SP1 and SP15 at both ends among the positions SP1 to SP15. Specifically, the maximum scanning angle is an angle formed between the line L1 connecting the focus F1 at the position SP1 and the center point CP and a line L15 connecting the focus F15 at the position SP15 and the center point CP.

In one tomosynthesis imaging operation, the radiation tubes 27 are driven one by one in the order of the radiation tube 27 at the position SP1, the radiation tube 27 at the position SP2, . . . , the radiation tube 27 at the position SP14, and the radiation tube 27 at the position SP15 to irradiate the breast M with the radiation 37. The radiation detector 26 detects the radiation 37 emitted at each of the positions SP1 to SP15 whenever the radiation 37 is emitted and outputs projection images at the positions SP1 to SP15. The tomosynthesis imaging can be performed by both the CC imaging method illustrated in FIG. 6 and the MLO imaging method illustrated in FIG. 7. In the case of simple imaging in which the CC imaging illustrated in FIG. 6 and the MLO imaging illustrated in FIG. 7 are independently performed, the radiation tube 27 at the position SP8 where the irradiation angle is 0° is used.

Figure 9:
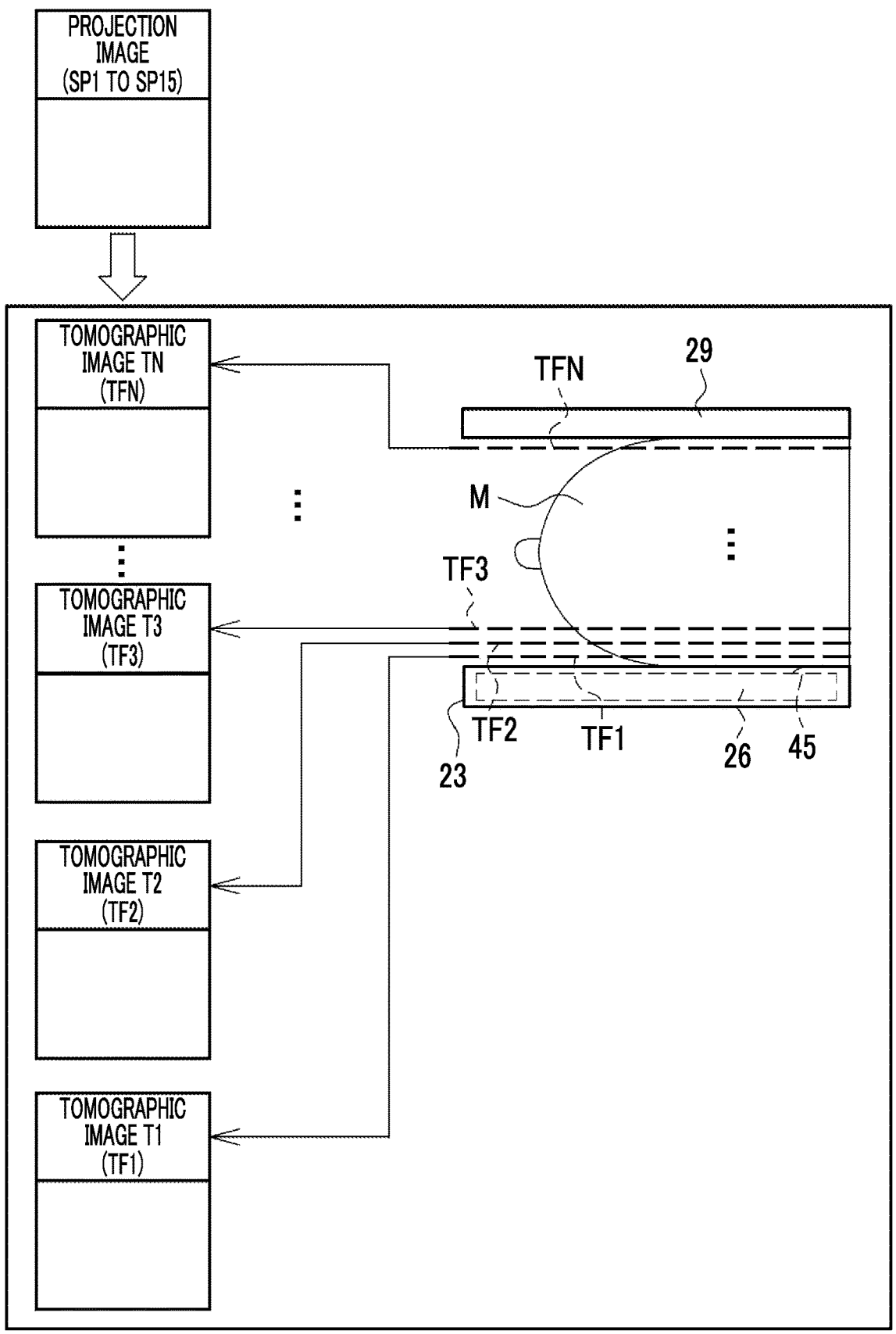
FIG. 9 is a diagram illustrating an aspect in which tomographic images are generated from a plurality of projection images obtained by the tomosynthesis imaging.

As illustrated in FIG. 9, the mammography apparatus 10 generates tomographic images T1 to TN corresponding to any tomographic planes TF1 to TFN of the breast M from the plurality of projection images at the plurality of positions SP1 to SP15 obtained by the tomosynthesis imaging illustrated in FIG. 8. The mammography apparatus 10 generates the tomographic images T1 to TN using a known method such as a filtered back projection method. In the tomographic images T1 to TN, structures in the tomographic planes TF1 to TFN have been highlighted.

Figure 10:
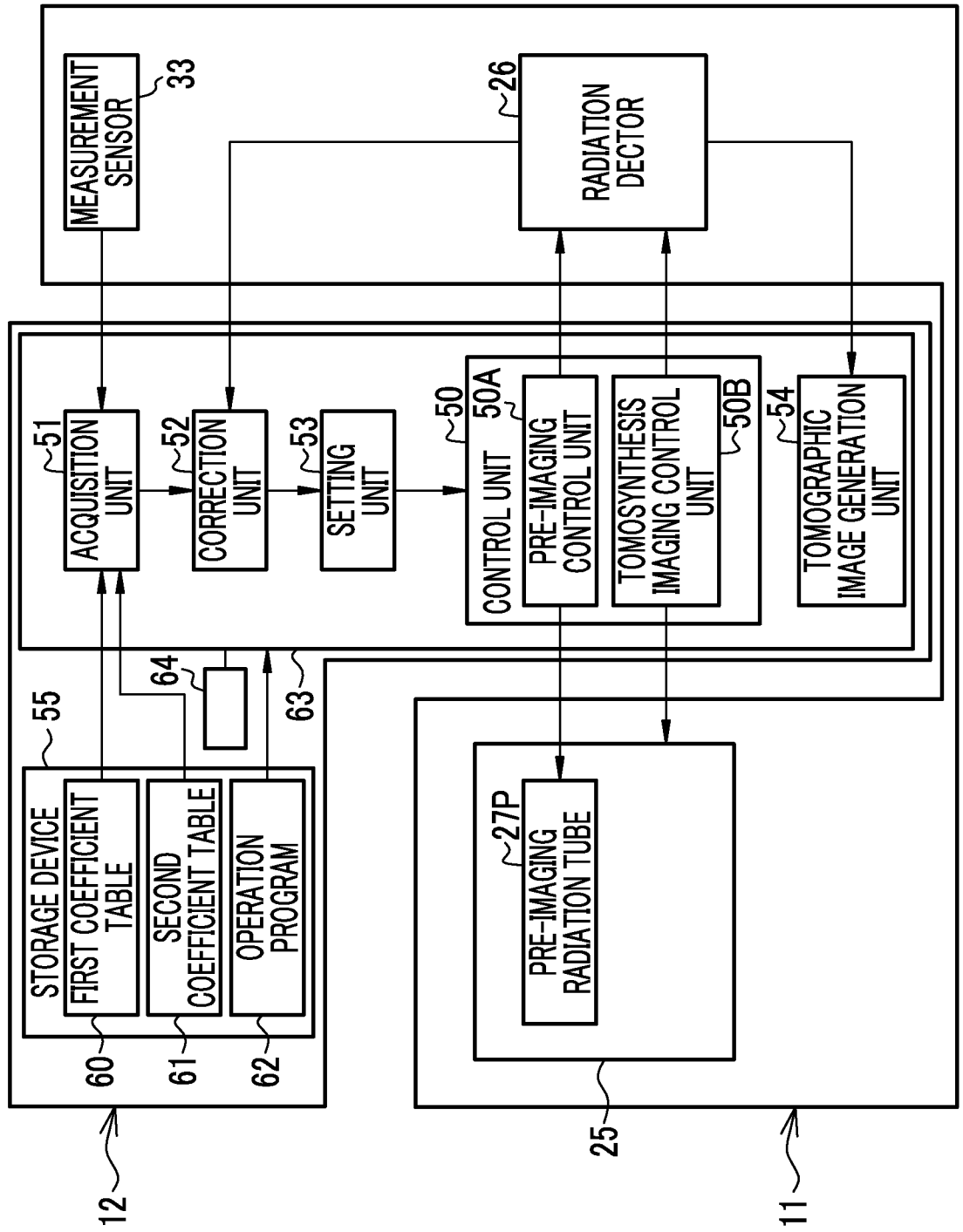
FIG. 10 is a block diagram illustrating a control device.

In FIG. 10, the control device 12 comprises, for example, a control unit 50, an acquisition unit 51, a correction unit 52, a setting unit 53, a tomographic image generation unit 54, and a storage device 55. The storage device 55 is, for example, a hard disk drive. The storage device 55 stores a first coefficient table 60, a second coefficient table 61, and an operation program 62.

The operation program 62 is an example of "a program for operating a tomosynthesis imaging apparatus" according to the technology of the present disclosure. In a case in which the operation program 62 is run, a central processing unit (CPU) of the control device 12 functions as the control unit 50, the acquisition unit 51, the correction unit 52, the setting unit 53, and the tomographic image generation unit 54 in cooperation with, for example, a memory 64. In addition, for example, a CPU 63 and the memory 64 are an example of a "computer" according to the technology of the present disclosure.

The control unit 50 controls the operation of the radiation source 25 and the radiation detector 26. The control unit 50 is provided with a pre-imaging control unit 50A and a tomosynthesis imaging control unit 50B. The pre-imaging control unit 50A performs pre-imaging using a pre-imaging radiation tube 27P. The pre-imaging radiation tube 27P is one radiation tube selected from the radiation tubes 27 disposed at the positions SP1 to SP15. The pre-imaging control unit 50A drives the pre-imaging radiation tube 27P according to irradiation conditions for pre-imaging such that the pre-imaging radiation tube 27P emits the radiation 37. Then, the pre-imaging control unit 50A outputs a projection image detected by the radiation detector 26 from the radiation detector 26 to the correction unit 52.

The acquisition unit 51 acquires a first coefficient from the first coefficient table 60. The first coefficient is a value corresponding to the compression thickness Th. The compression thickness Th is input from the measurement sensor 33 to the acquisition unit 51. The acquisition unit 51 acquires the first coefficient corresponding to the compression thickness Th output from the measurement sensor 33 from the first coefficient table 60. In addition, the acquisition unit 51 acquires a second coefficient from the second coefficient table 61. The acquisition unit 51 outputs the acquired first and second coefficients to the correction unit 52.

The correction unit 52 corrects the irradiation conditions for pre-imaging using the first and second coefficients from the acquisition unit 51. In addition, the correction unit 52 analyzes the projection image from the radiation detector 26 in pre-imaging and temporarily sets irradiation conditions for tomosynthesis imaging. The correction unit 52 corrects the temporarily set irradiation conditions for tomosynthesis imaging using the first and second coefficients from the acquisition unit 51. The correction unit 52 outputs the corrected irradiation conditions to the setting unit 53.

The setting unit 53 sets the irradiation conditions corrected by the correction unit 52 in the radiation source 25. Specifically, the setting unit 53 outputs the corrected irradiation conditions for pre-imaging from the correction unit 52 to the pre-imaging control unit 50A such that the corrected irradiation conditions for pre-imaging are set in the pre-imaging radiation tube 27P. In addition, the setting unit 53 outputs the corrected irradiation conditions for tomosynthesis imaging from the correction unit 52 to the tomosynthesis imaging control unit 50B such that the corrected irradiation conditions for tomosynthesis imaging are set in each radiation tube 27.

The irradiation conditions include a tube voltage applied to the radiation tube 27 and a tube current-irradiation time product. The tube current-irradiation time product is literally the product of a tube current flowing through the radiation tube 27 and the irradiation time of the radiation 37. In addition, in some cases, the irradiation conditions are expressed as a necessary radiation dose of the radiation tube 27 at the position SP8 where the irradiation angle is 0°.

The temporary setting of the irradiation conditions for tomosynthesis imaging corrected by the correction unit 52 is, for example, increasing the tube current-irradiation time product from the rated value in a case in which the thickness of the breast M is relatively large and the density of the projection image from the radiation detector 26 is lower than a desired level. As such, in a case in which the irradiation conditions for tomosynthesis imaging based on the pre-imaging is temporarily set, the density level of the projection image captured by the tomosynthesis imaging and the tomographic image T generated by the projection image is substantially constant regardless of the individual difference in the breast M.

The tomosynthesis imaging control unit 50B performs the tomosynthesis imaging illustrated in FIG. 9 using all of the radiation tubes 27 disposed at the positions SP1 to SP15. Specifically, the tomosynthesis imaging control unit 50B drives each of the radiation tubes 27 under the irradiation conditions set by the setting unit 53 such that the radiation tubes 27 sequentially emit the radiation 37 to the breast M. Then, a plurality of projection images detected by the radiation detector 26 are output from the radiation detector 26 to the tomographic image generation unit 54.

As illustrated in FIG. 9, the tomographic image generation unit 54 generates tomographic images T on the basis of the plurality of projection images from the radiation detector 26. The tomographic image generation unit 54 transmits the generated tomographic images T to the image DB server 14 through the network 13.

As illustrated in FIG. 11, in the first coefficient table 60, a first coefficient Kfp(i, Thj) is registered for each of the plurality of radiation tubes 27 disposed at the positions SP1 to SP15. Here, i is a number for identifying the radiation tube 27 and numbers 1 to 15 corresponding to the positions SP1 to SP15 are assigned to the radiation tubes 27. The compression thickness Thj is set at an interval of 1 mm in the range of, for example, 10 mm to 80 mm. In addition, j is a number for identifying each compression thickness. In the above-mentioned example in which the compression thickness Thj is set at an interval of 1 mm in the range of 10 mm to 80 mm, j is in the range of 1 to 71. The first coefficient Kfp(i, Thj) is a coefficient indicating the rate of change in the arrival dose of the radiation 37 depending on the irradiation angle which corresponds to the compression thickness Thj.

As illustrated in FIG. 12, in the second coefficient table 61, a second coefficient Kmd(i) is registered for each of the plurality of radiation tubes 27 disposed at the positions SP1 to SP15. The second coefficient Kmd(i) is related to the dose of the radiation 37.

Here, the "radiation dose" is the dose of the radiation 37 emitted from the radiation tube 27. The "radiation dose" is ideally a dose measured by a dosimeter immediately below the radiation tube 27. In contrast, the "arrival dose" is a dose of the radiation 37 that is emitted from the radiation tube 27, is transmitted through the breast M, and finally reaches the imaging surface 45 of the radiation detector 26. Therefore, the arrival dose is naturally less than the radiation dose under the same irradiation conditions.

Figure 13:
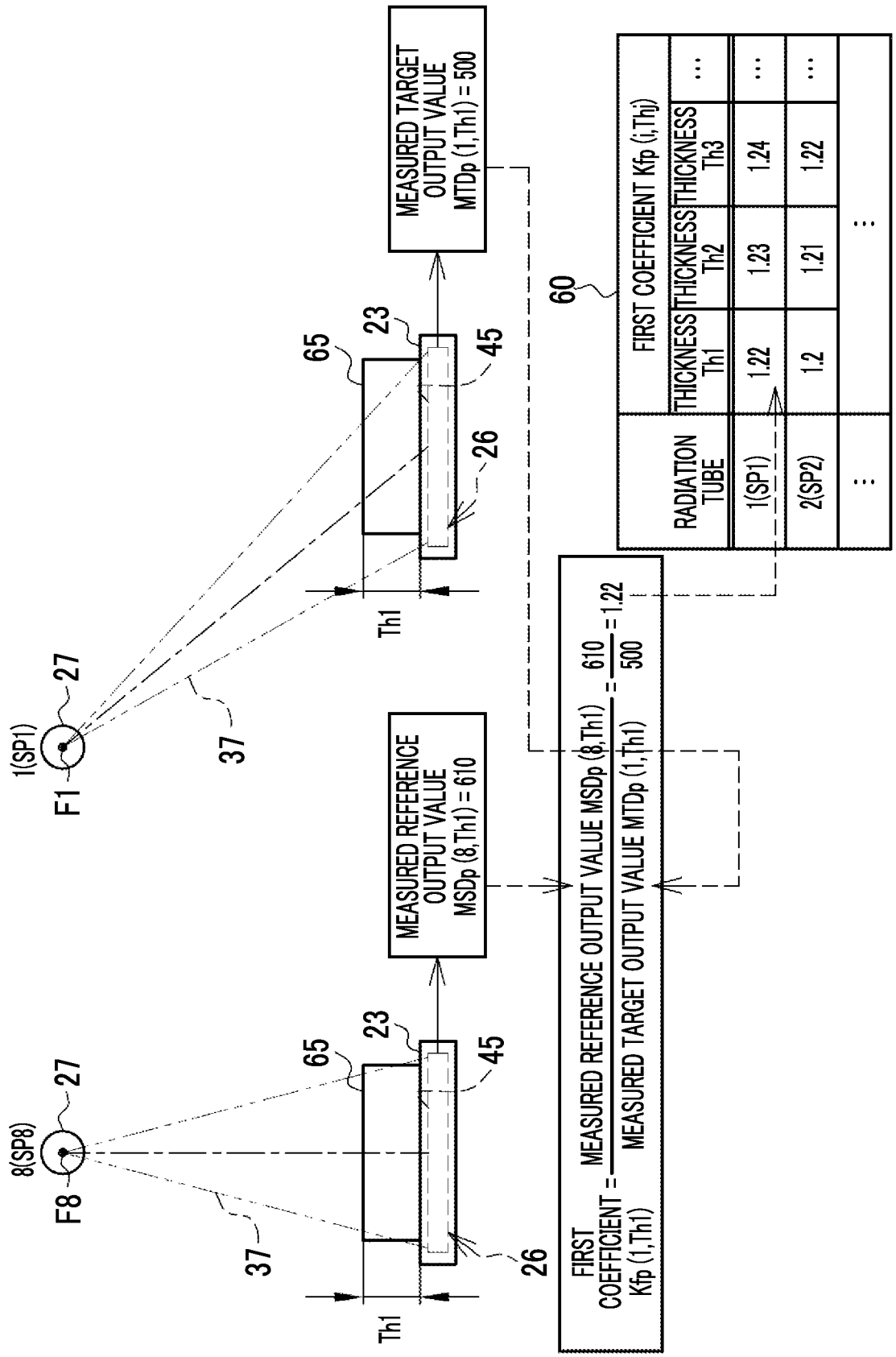
FIG. 13 is a diagram illustrating an aspect in which a first coefficient is calculated.

The first coefficient Kfp(i, Thj) is calculated before the mammography apparatus 10 is shipped. Specifically, as illustrated in FIG. 13, the first coefficient Kfp(i, Thj) is calculated by providing each radiation tube 27 in the radiation source 25 and then placing a phantom 65 on the detector accommodation portion 23. The phantom 65 is a model that represents the breast M in a pseudo manner and is made of, for example, an acrylic resin. The phantom 65 is prepared for each compression thickness Thj.

First, the radiation 37 is emitted from the radiation tube 27 disposed at the position SP8 where the irradiation angle is 0° and a measured reference output value MSDp(8, Thj) actually output by the radiation detector 26 is obtained. The position SP8 where the irradiation angle is 0° is an example of a "reference position" according to the technology of the present disclosure. In addition, the reference position is not limited to the position SP8 where the irradiation angle is 0°. The reference position may be a position in a predetermined irradiation angle range, for example, a position in an irradiation angle range of −10° to +10°.

Similarly, the radiation 37 is emitted from the radiation tube 27 of which the first coefficient Kfp(i, Thj) is to be calculated and a measured target output value MTDp(i, Thj) actually output by the radiation detector 26 is obtained. The measured reference output value MSDp(8, Thj) and the measured target output value MTDp(i, Thj) are, for example, an average value of all of the output values from the radiation detector 26 or an average value of the output values in a specific region of the imaging surface 45 of the radiation detector 26. The specific region is, for example, a central region of the imaging surface 45.

The first coefficient Kfp(i, Thj) is calculated by dividing the measured reference output value MSDp(8, Thj) by the measured target output value MTDp(i, Thj). The calculated first coefficient Kfp(i, Thj) is registered in the first coefficient table 60 and is stored in the storage device 55. The first coefficient Kfp(8, Thj) of the radiation tube 27 disposed at the position SP8 where the irradiation angle is 0° is 1, which is natural from the method of calculating the first coefficient Kfp(i, Thj).

FIG. 13 illustrates a case in which j is 1 and the radiation tube 27 of which the first coefficient Kfp(i, Thj) is to be calculated is the radiation tube 27 disposed at the position SP1 (i=1). In addition, FIG. 13 illustrates a case in which the measured reference output value MSDp(8, Th1) is 610 and the measured target output value MTDp(1, Th1) is 500. In this case, the first coefficient Kfp(1, Th1) is 610/500=1.22.

Figure 14:
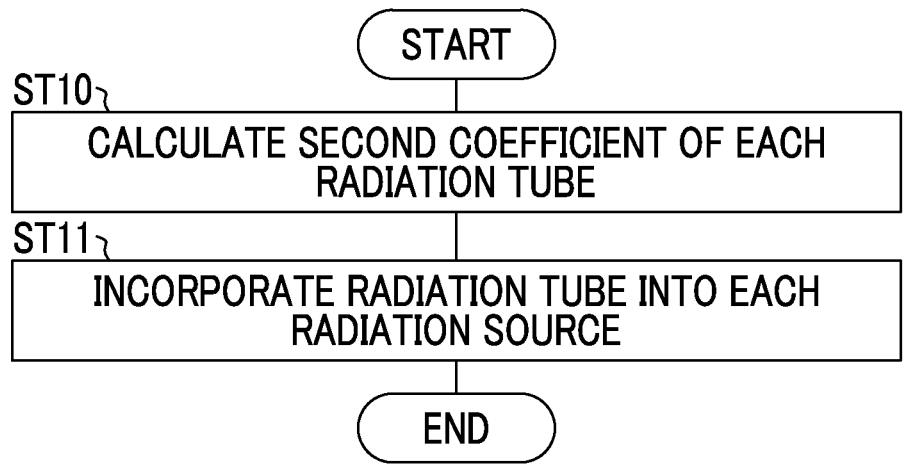
FIG. 14 is a diagram illustrating a first pattern in which a second coefficient is calculated.
Figure 15:
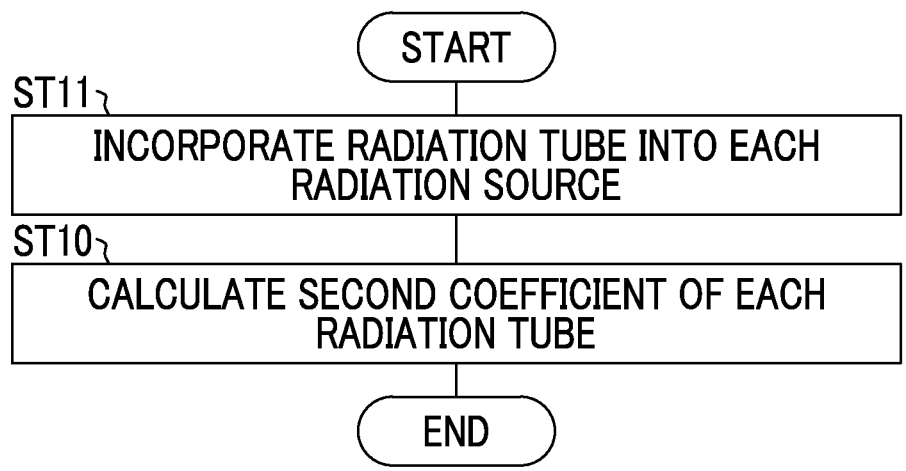
FIG. 15 is a diagram illustrating a second pattern in which the second coefficient is calculated.

The second coefficient Kmd(i) is also calculated before the mammography apparatus 10 is shipped. However, there are two patterns for calculating the second coefficient Kmd (i). The first pattern is a method which calculates the second coefficient Kmd(i) of each radiation tube 27 (Step ST10) and incorporates each radiation tube 27 into the radiation source 25 (Step ST11) as illustrated in FIG. 14. The second pattern is a method which incorporates each radiation tube 27 into the radiation source 25 (Step ST11) and calculates the second coefficient Kmd(i) of each radiation tube 27 (Step ST10) as illustrated in FIG. 15, contrary to the first pattern.

Figure 16:
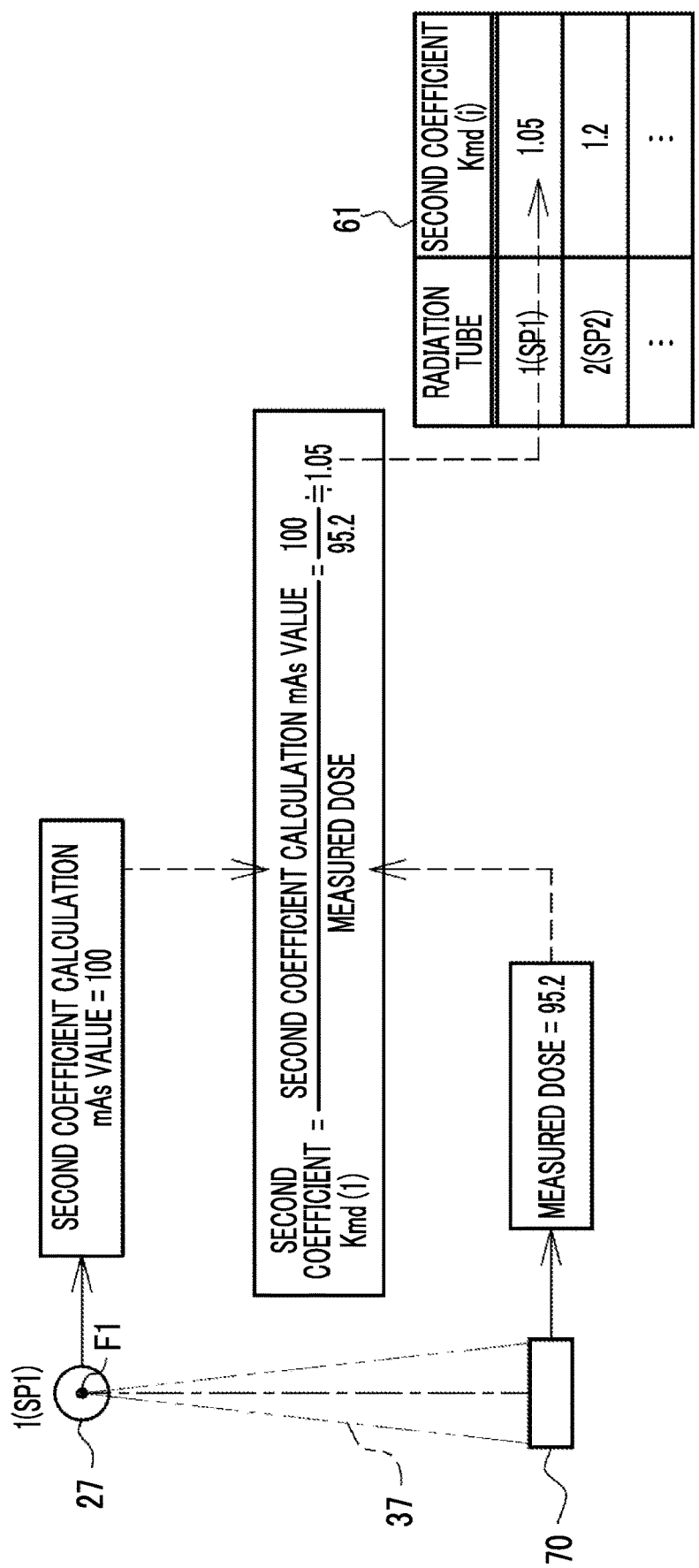
FIG. 16 is a diagram illustrating an aspect in which the second coefficient is calculated.

The calculation of the second coefficient Kmd(i) is common to the methods of the first pattern and the second pattern. That is, as illustrated in FIG. 16, a second coefficient calculation mAs value is set as the irradiation condition in the radiation tube 27 of which the second coefficient Kmd(i) is to be calculated. Then, a dosimeter 70 measures the dose of the radiation 37 emitted according to the second coefficient calculation mAs value.

The second coefficient Kmd(i) is calculated by dividing the second coefficient calculation mAs value by the dose measured by the dosimeter 70. That is, the second coefficient Kmd(i) is a tube current-irradiation time product per unit dose. The calculated second coefficient Kmd(i) is registered in the second coefficient table 61 and is stored in the storage device 55.

FIG. 16 illustrates a case in which the radiation tube 27 of which the second coefficient Kmd(i) is to be calculated is the radiation tube 27 disposed at the position SP1 (i=1). In addition, FIG. 16 illustrates a case in which the second coefficient calculation mAs value is 100 and the measured dose is 95.2. In this case, the second coefficient Kmd(1) is 100/95.2≈1.05.

In the case of the first pattern in which, after the second coefficient Kmd(i) of each radiation tube 27 is calculated, each radiation tube 27 is incorporated in the radiation source 25 as illustrated in FIG. 14, each radiation tube 27 is set at the position where the positional relationship with the dosimeter 70 is the same and the dose of radiation is measured. The position where the positional relationship with the dosimeter 70 is the same is, for example, the position which confronts a measurement surface of the dosimeter 70 and where the irradiation angle is 0°.

Figure 17:
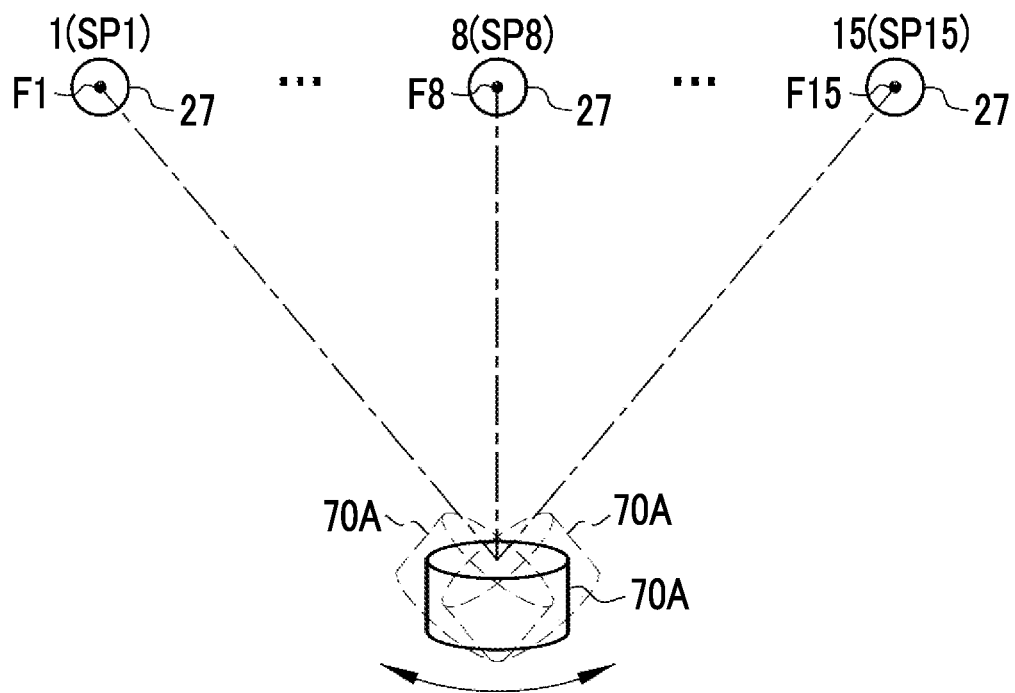
FIG. 17 is a diagram illustrating a case in which an ionization chamber is used as a dosimeter in order to calculate the second coefficient.
Figure 18:
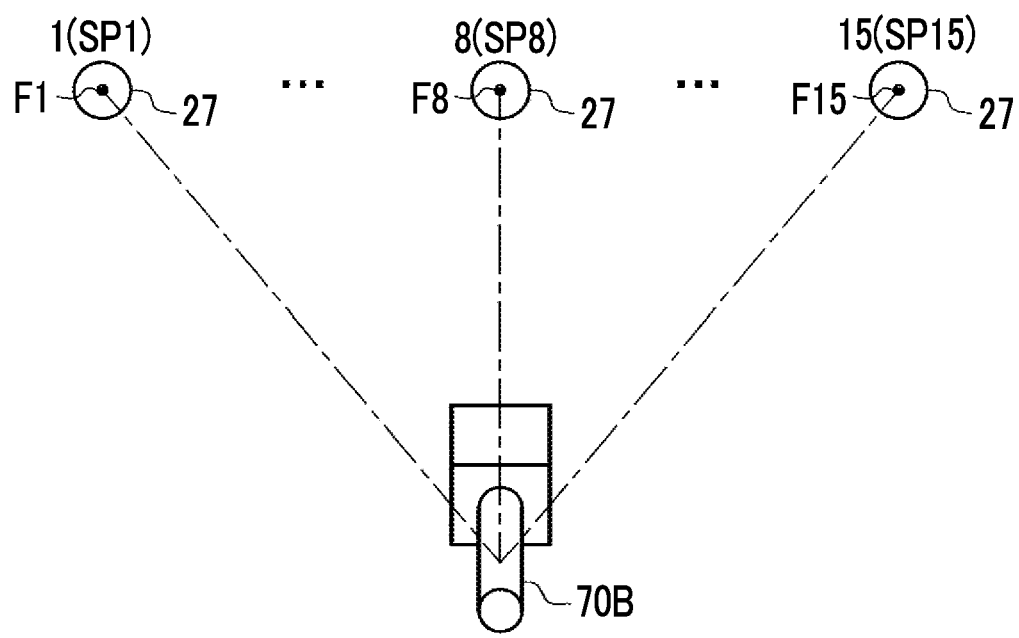
FIG. 18 is a diagram illustrating a case in which a cylindrical semiconductor dosimeter is used as the dosimeter in order to calculate the second coefficient.
Figure 19:
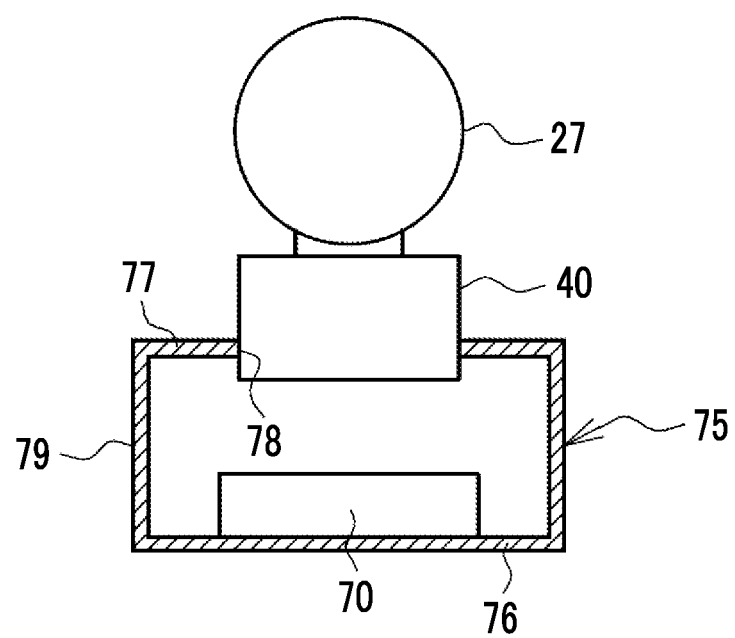
FIG. 19 is a diagram illustrating a case in which a jig is used in order to calculate the second coefficient.

In contrast, in the case of the second pattern in which, after each radiation tube 27 is incorporated in the radiation source 25, the second coefficient Kmd(i) of each radiation tube 27 is calculated as illustrated in FIG. 15, the dose of radiation is measured by any of the methods illustrated in FIGS. 17 to 19.

FIG. 17 illustrates a case in which an ionization chamber 70A is used as the dosimeter. In this case, the ionization chamber 70A is rotated such that a measurement surface of the ionization chamber 70A confronts the radiation tube 27 of which the second coefficient Kmd(i) is to be calculated and the dose of radiation is measured.

FIG. 18 illustrates a case in which a cylindrical semiconductor dosimeter 70B is used as the dosimeter. The cylindrical semiconductor dosimeter 70B is a dosimeter used in a computed tomography (CT) imaging apparatus and has the same sensitivity in all directions. Therefore, the cylindrical semiconductor dosimeter 70B does not need to be rotated such that a measurement surface confronts the radiation tube 27, unlike the ionization chamber 70A illustrated in FIG. 17.

FIG. 19 illustrates a case in which a jig 75 for measuring the dose of radiation as directly below the radiation tube 27 as possible is used. The jig 75 has a rectangular parallelepiped shape and a dosimeter 70 is attached to the center of the inner wall surface of a bottom plate 76. An attachment hole 78 is provided in a top plate 77 of the jig 75. The irradiation field limiter 40 is detachably attached to the attachment hole 78. A side plate 79 of the jig 75 has a height of, for example, several centimeters to several tens of centimeters. In this case, the jig 75 is attached to the irradiation field limiter 40 of the radiation tube 27 of which the second coefficient Kmd(i) is to be calculated. Then, the dosimeter 70 measures the dose of the radiation 37 emitted according to the second coefficient calculation mAs value. In the first pattern illustrated in FIG. 14, a jig for measuring a dose of radiation immediately below the radiation tube 27, such as the jig 75, may be used.

As illustrated in FIGS. 20A and 20B, the correction unit 52 corrects the irradiation conditions using the first coefficient Kfp(i, Thj). In addition, the correction unit 52 corrects the irradiation conditions using the second coefficient Kmd (i) in addition to the first coefficient Kfp(i, Thj).

FIG. 20A illustrates an aspect in which the irradiation conditions are corrected in pre-imaging. The correction unit 52 calculates a pre-imaging mAs value PB(i) as represented by the following Expression (A):

$$PB(i)=PDf0 \times Kfp(i, Thj) \times Kmd(i) \qquad (A).$$

That is, the correction unit 52 corrects the tube current-irradiation time product included in the irradiation conditions.

In addition, PDf0 is a preset irradiation condition for pre-imaging and is a necessary dose of radiation in a case in which the radiation tube 27 disposed at the position SP8 where the irradiation angle is 0° is a pre-imaging radiation tube 27P.

FIG. 20B illustrates an aspect in which the irradiation conditions are corrected in tomosynthesis imaging. The correction unit 52 calculates a tomosynthesis imaging mAs value TB(i) as represented by the following Expression (B):

$$TB(i)=TDf0 \times Kfp(i, Thj) \times Kmd(i) \qquad (B).$$

That is, the correction unit 52 corrects the tube current-irradiation time product included in the irradiation conditions.

In addition, TDf0 is an irradiation condition for tomosynthesis imaging which is temporarily set on the basis of the result of pre-imaging and is a necessary dose of radiation which is emitted from the radiation tube 27 disposed at the position SP8 where the irradiation angle is 0° in tomosynthesis imaging.

As illustrated in FIG. 21, the acquisition unit 51 acquires the first coefficient Kfp(i, Thj) corresponding to the number of the pre-imaging radiation tube 27P and the compression thickness Th from the measurement sensor 33 from the first coefficient table 60. In addition, the acquisition unit 51 acquires the second coefficient Kmd(i) corresponding to the number of the pre-imaging radiation tube 27P from the second coefficient table 61. The correction unit 52 multiplies the preset irradiation condition PDf0 for pre-imaging by the first coefficient Kfp(i, Thj) and the second coefficient Kmd(i) from the acquisition unit 51 to calculate the pre-imaging mAs value PB(i).

FIG. 21 illustrates a case in which the pre-imaging radiation tube 27P is the radiation tube 27 disposed at the position SP1, the compression thickness is Th2, and the irradiation condition PDf0 for pre-imaging is 50. In this case, Kfp(1, Th2) is 1.23 and Kmd(1) is 1.05. Therefore, the pre-imaging mAs value PB(1) is as follows:

$$PB(1) = PDf0 \times Kfp(1, Th2) \times Kmd(1) = 50 \times 1.23 \times 1.05 \approx 64.58.$$

In the example illustrated in FIG. 21, the pre-imaging radiation tube 27P is the radiation tube 27 disposed at the position SP1. However, the invention is not limited thereto. The pre-imaging radiation tube 27P may be the radiation tube 27 disposed at the position SP8 where the irradiation angle is 0°. In this case, since the first coefficient Kfp(8, Thj) of the radiation tube 27 disposed at the position SP8 where the irradiation angle is 0° is 1, Expression (A) is rewritten as the following Expression (C):

$$PB(8) = PDf0 \times Kmd(8) \qquad (C).$$

Figure 22:
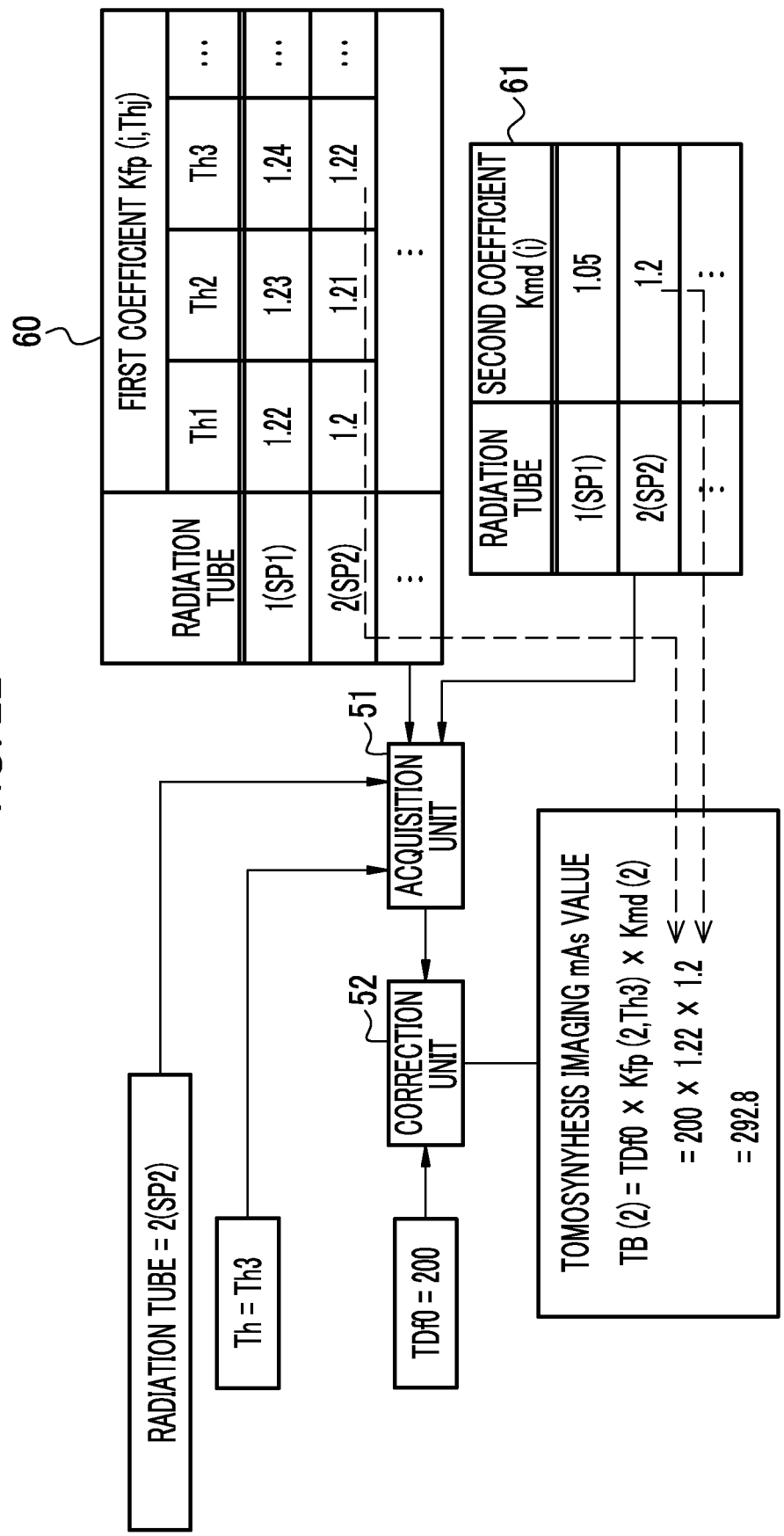
FIG. 22 is a diagram illustrating an aspect in which the correction unit calculates a tomosynthesis imaging mAs value.

As illustrated in FIG. 22, the acquisition unit 51 acquires the first coefficient Kfp(i, Thj) corresponding to the number of the radiation tube 27 and the compression thickness Th from the measurement sensor 33 from the first coefficient table 60. In addition, the acquisition unit 51 acquires the second coefficient Kmd(i) corresponding to the number of the radiation tube 27 from the second coefficient table 61. The correction unit 52 multiplies the irradiation condition TDf0 for tomosynthesis imaging which has been temporarily set on the basis of the result of pre-imaging by the first coefficient Kfp(i, Thj) and the second coefficient Kmd(i) from the acquisition unit 51 to calculate a tomosynthesis imaging mAs value TB(i).

FIG. 22 illustrates a case in which the radiation tube 27 is a radiation tube disposed at the position SP2, the compression thickness is Th3, and the irradiation condition TDf0 for tomosynthesis imaging is 200. In this case, Kfp(2, Th3) is 1.22 and Kmd(2) is 1.2. Therefore, the tomosynthesis imaging mAs value TB(2) is as follows:

$$TB(2) = TDf0 \times Kfp(2, Th3) \times Kmd(2) = 200 \times 1.22 \times 1.2 = 292.8.$$

Figure 23:
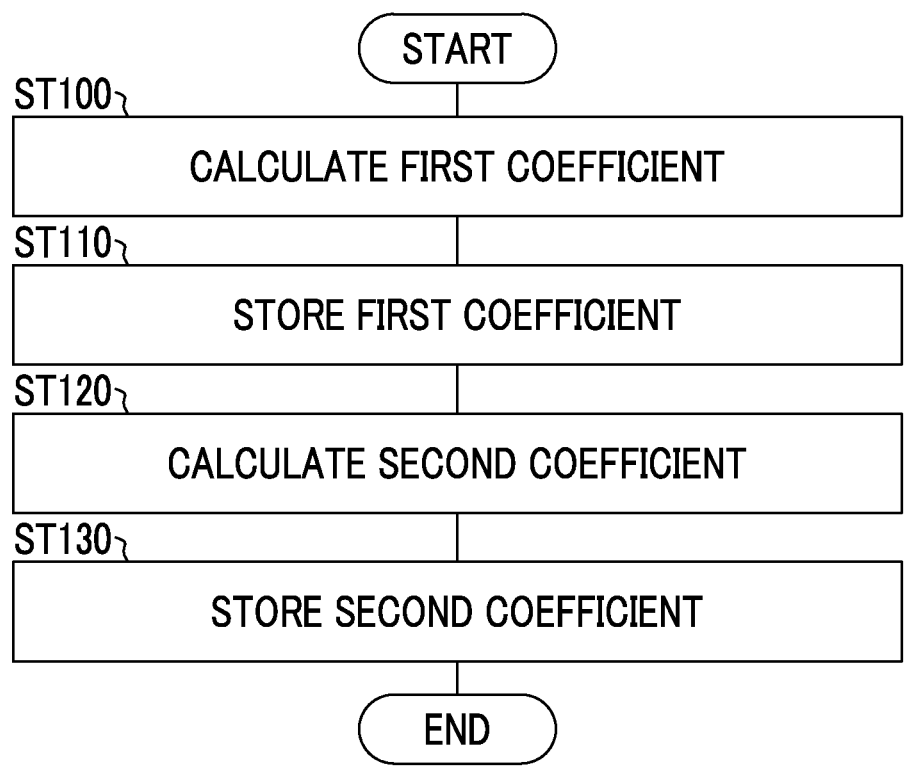
FIG. 23 is a flowchart illustrating the procedure of a process before the mammography apparatus is shipped.

Next, the operation of the above-mentioned configuration will be described with reference to flowchart illustrated in FIGS. 23 and 24. First, as illustrated in FIG. 23, before the mammography apparatus 10 is shipped, the first coefficient Kfp(i, Thj) is calculated as illustrated in FIG. 13 (Step ST100). The calculated first coefficient Kfp(i, Thj) is registered in the first coefficient table 60 and is stored in the storage device 55 (Step ST110). In addition, the first coefficient Kfp(i, Thj) may not be stored in a table format, but may be stored in a function format.

Similarly, before the mammography apparatus 10 is shipped, the second coefficient Kmd(i) is calculated as illustrated in FIGS. 14 to 19 (Step ST120). The calculated second coefficient Kmd(i) is registered in the second coefficient table 61 and is stored in the storage device 55 (Step ST130). In addition, after the second coefficient Kmd(i) is calculated and stored, the first coefficient Kfp(i, Thj) may be calculated and stored.

Figure 24:
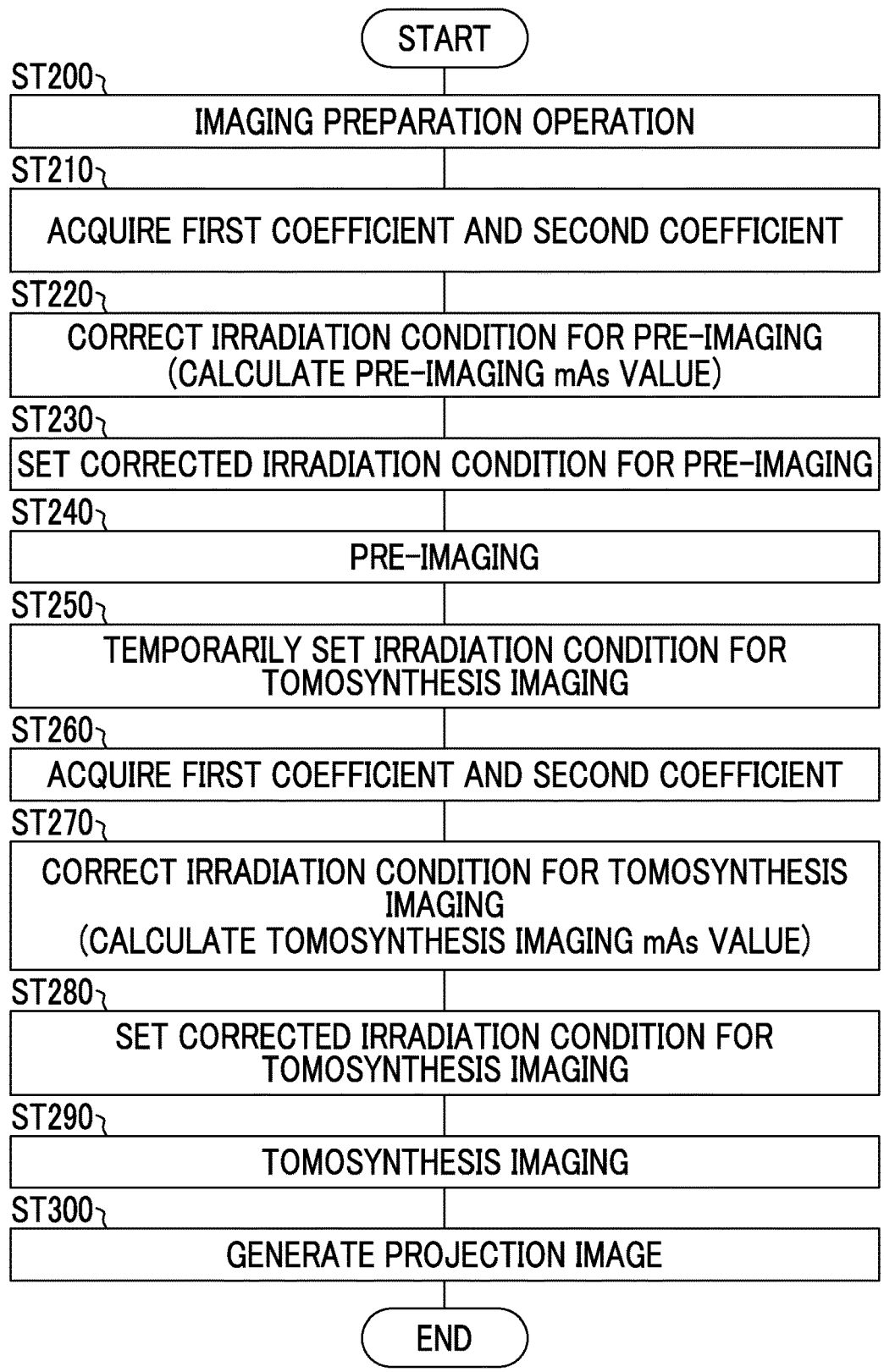
FIG. 24 is a flowchart illustrating the procedure of a tomosynthesis imaging process of the mammography apparatus.

As illustrated in FIG. 24, the procedure of tomosynthesis imaging in a first imaging mode of the mammography apparatus 10 starts from an imaging preparation operation in Step ST200. The imaging preparation operation is performed by a radiology technician and is mainly related to the positioning of the breast. For example, the imaging preparation operation includes an operation that guides the subject H in front of the apparatus main body 11, places the breast M on the detector accommodation portion 23, moves the compression plate 29 to the detector accommodation portion 23, and compresses the breast M interposed between the compression plate 29 and the detector accommodation portion 23. After the imaging preparation operation ends, the radiology technician inputs a command to start tomosynthesis imaging.

As illustrated in FIG. 21, the acquisition unit 51 acquires the first coefficient Kfp(i, Thj) corresponding to the number of the pre-imaging radiation tube 27P and the compression thickness Th from the measurement sensor 33 from the first coefficient table 60. In addition, the acquisition unit 51 acquires the second coefficient Kmd(i) corresponding to the number of the pre-imaging radiation tube 27P from the second coefficient table 61 (Step ST210, an acquisition step). The first coefficient Kfp(i, Thj) and the second coefficient Kmd(i) are output from the acquisition unit 51 to the correction unit 52.

As illustrated in Step ST220, the correction unit 52 corrects the irradiation condition for pre-imaging (correction step). Specifically, as illustrated in FIG. 20A and FIG. 21, the correction unit 52 calculates the pre-imaging mAs value PB(i) using the first coefficient Kfp(i, Thj) and the second coefficient Kmd(i) from the acquisition unit 51. The calculated pre-imaging mAs value PB(i) is output from the correction unit 52 to the setting unit 53 and is output from the setting unit 53 to the pre-imaging control unit 50A. Then, the corrected irradiation condition for pre-imaging is set in the pre-imaging radiation tube 27P (Step ST230, a setting step). Then, as illustrated in Step ST240, the pre-imaging control unit 50A gives the pre-imaging mAs value PB(i) to the pre-imaging radiation tube 27P to perform pre-imaging.

The projection image output from the radiation detector 26 in pre-imaging is input to the correction unit 52. The correction unit 52 temporarily sets the irradiation condition for tomosynthesis imaging on the basis of the projection image from the radiation detector 26 (Step ST250).

As illustrated in FIG. 22, the acquisition unit 51 acquires the first coefficient Kfp(i, Thj) corresponding to the number of the radiation tube 27 and the compression thickness Th from the measurement sensor 33 from the first coefficient table 60. In addition, the acquisition unit 51 acquires the second coefficient Kmd(i) corresponding to the number of the radiation tube 27 from the second coefficient table 61 (Step ST260, an acquisition step). The first coefficient Kfp(i, Thj) and the second coefficient Kmd(i) are output from the acquisition unit 51 to the correction unit 52.

The correction unit 52 corrects the temporarily set irradiation condition for tomosynthesis imaging (Step ST270, a correction step). Specifically, as illustrated in FIG. 20B and FIG. 22, the correction unit 52 calculates the tomosynthesis imaging mAs value TB(i) using the first coefficient Kfp(i, Thj) and the second coefficient Kmd(i) from the acquisition unit 51. The calculated tomosynthesis imaging mAs value TB(i) is output from the correction unit 52 to the setting unit 53 and is output from the setting unit 53 to the tomosynthesis imaging control unit 50B. Then, the corrected irradiation condition for tomosynthesis imaging is set in each radiation tube 27 (Step ST280, a setting step). Then, as illustrated in Step ST290, the tomosynthesis imaging control unit 50B gives the tomosynthesis imaging mAs value TB(i) to each radiation tube 27 to perform the tomosynthesis imaging illustrated in FIG. 8.

The projection image output from the radiation detector 26 in the tomosynthesis imaging is output to the tomographic image generation unit 54. The tomographic image generation unit 54 generates the tomographic image T on the basis of the projection image from the radiation detector 26 as illustrated in FIG. 9 (Step ST300). The generated tomographic image T is transmitted from the tomographic image generation unit 54 to the image DB server 14.

The correction unit 52 corrects the irradiation condition using the first coefficient Kfp(i, Thj) indicating the rate of change in the arrival dose of the radiation 37 depending on the irradiation angle. Therefore, in a case in which the radiation 37 is emitted from a plurality of radiation tubes 27 at different irradiation angles, it is possible to correct the arrival dose of the radiation 37 so to be the same regardless of the irradiation angle. In addition, the correction unit 52 corrects the irradiation condition using the second coefficient Kmd(i) related to the dose of the radiation 37 for each of the plurality of radiation tubes 27. Therefore, it is possible to correct the dose of the radiation 37 so to be the same regardless of the individual difference between the plurality of radiation tubes 27.

Specifically, as illustrated in FIG. 25, before correction, the output values of the radiation detector 26 by each radiation tube 27 are different from each other due to a change in the arrival dose of the radiation 37 depending the irradiation angle and a change in the dose of the radiation 37 depending on the difference between the plurality of radiation tubes 27. However, after correction, the output values of the radiation detector 26 by each radiation tube 27 are equal to each other.

As such, correction is performed using the first coefficient Kfp(i, Thj) such that the arrival dose of the radiation 37 is the same. Therefore, in pre-imaging, even in a case in which the pre-imaging radiation tube 27P is any radiation tube 27, it is possible to obtain much the same effect. In addition, in the tomosynthesis imaging, the projection images have nearly the same quality. Therefore, it is possible to improve the quality of the tomographic image T generated on the basis of the projection image.

In addition, correction is performed using the second coefficient Kmd(i) such that the dose of the radiation 37 is the same. Therefore, it is possible to obtain the same result of pre-imaging regardless of whether the pre-imaging radiation tube 27P is any radiation tube 27. Further, it is possible to further improve the quality of the tomographic image T.

Correction using the second coefficient Kmd(i) is not essential. However, since the above-mentioned effect is improved by the correction using the second coefficient Kmd(i), it is preferable to perform the correction using the second coefficient Kmd(i).

In a case in which correction using the second coefficient Kmd(i) is not performed, the above-mentioned Expression (A) is rewritten as the following Expression (D) and the above-mentioned Expression (B) is rewritten as the following Expression (E):

$$PB(i)=PDf0 \times Kfp(i,Thj) \quad \text{(D); and}$$

$$TB(i)=TDf0 \times Kfp(i,Thj) \quad \text{(E).}$$

The first coefficient Kfp(i, Thj) is a value obtained by dividing the measured reference output value MSDp(i, Thj) which has been actually output by the radiation detector 26 receiving the radiation 37 emitted from the radiation tube 27 disposed at of which the irradiation angle is disposed at a reference position by the measured target output value MTDp(i, Thj) which has been actually output by the radiation detector 26 receiving the radiation 37 emitted from the radiation tube 27 of which the first coefficient Kfp(i, Thj) is to be calculated. Since the actual output value is used, it is possible to calculate the first coefficient Kfp(i, Thj) with high reliability.

In the radiation tubes 27, the focuses F1 to F15 of the radiation 37 are disposed at the plurality of positions SP1 to SP15 which are set so as to be linearly arranged at equal intervals D. Since the regularity of the arrangement positions SP1 to SP15 of the focuses F1 to F15 is ensured, it is possible to simplify the process related to the generation of the tomographic image T.

In addition, a configuration in which tomosynthesis imaging is performed without pre-imaging rather than the configuration in which pre-imaging is performed and tomosynthesis imaging is performed under the irradiation conditions based on the result of the pre-imaging. In this case, the radiology technician who operates the mammography apparatus 10 sets a total mAs value in the control device 12. The total mAs value is a mAs value that is given to one radiation tube in tomosynthesis imaging in a case in which the plurality of radiation tubes 27 are regarded as the one radiation tube.

Figure 26:
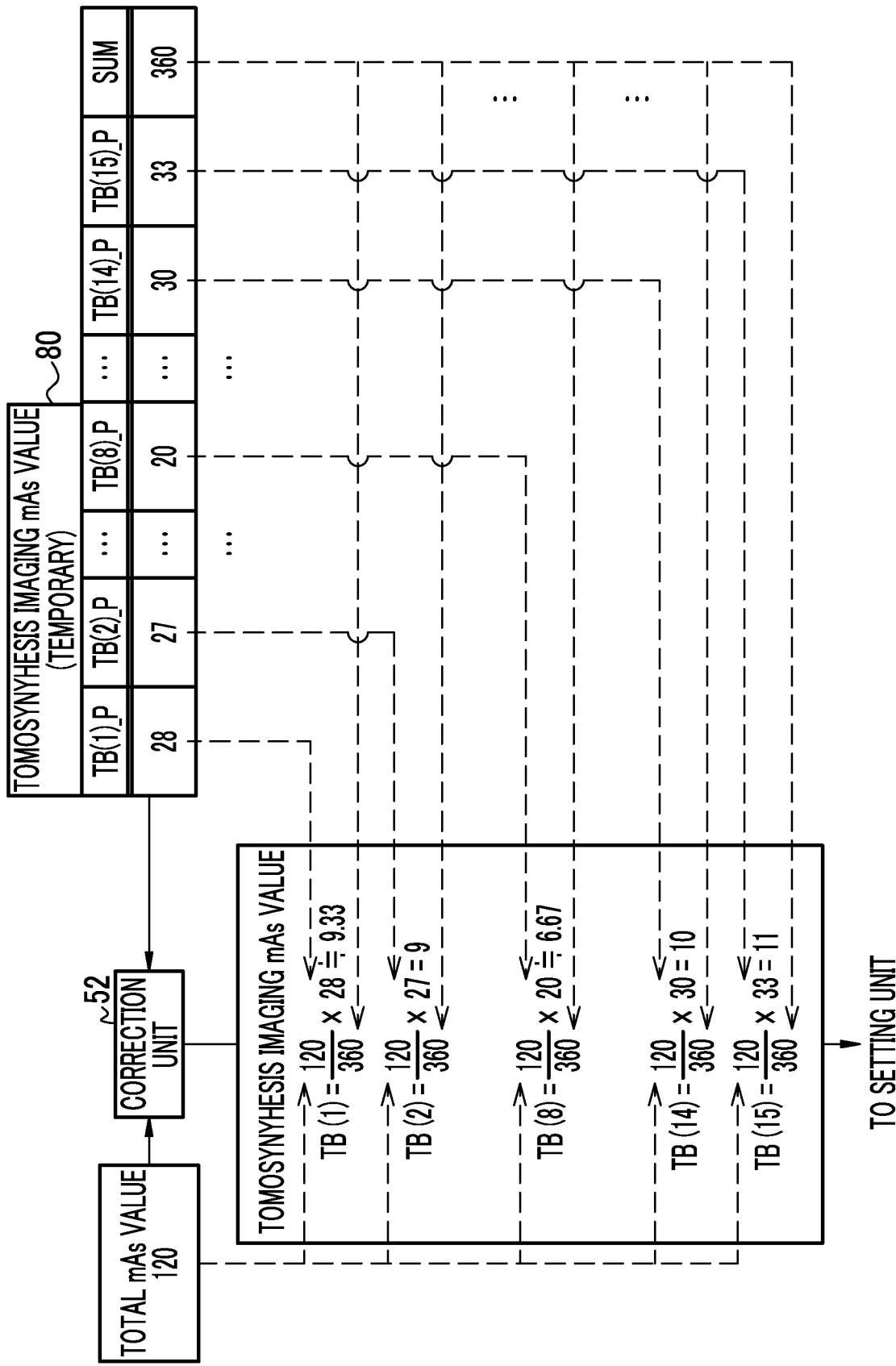
FIG. 26 is a diagram illustrating a method for setting the irradiation conditions in a case in which a total mAs value is set and tomosynthesis imaging is performed without pre-imaging.

In a case in which the total mAs value is set and tomosynthesis imaging is performed without pre-imaging, the irradiation conditions are set as illustrated in FIG. 26.

In FIG. 26, as illustrated in a table 80, the correction unit 52 substitutes an appropriate value into TDf0 to calculate a temporary tomosynthesis imaging mAs value TB(i)_P. In addition, the correction unit 52 calculates the sum of the temporary tomosynthesis imaging mAs values TB(i)_P.

The correction unit 52 divides the total mAs value by the sum of the temporary tomosynthesis imaging mAs values TB(i)_P. Then, the correction unit 52 multiplies the obtained value by the temporary tomosynthesis imaging mAs value TB(i)_P to calculate a tomosynthesis imaging mAs value TB(i).

FIG. 26 illustrates a case in which the total mAs value is 120 and the sum of the temporary tomosynthesis imaging mAs values TB(i)_P is 360. In this case, for example, since the temporary tomosynthesis imaging mAs value TB(2)_P is 27, the tomosynthesis imaging mAs value TB(2) of the radiation tube 27 disposed at the position SP2 is as follows:

$$TB(2)=(120/360) \times 27=9.$$

As such, in a case in which the total mAs value is set and tomosynthesis imaging is performed without pre-imaging, the total mAs value is distributed to each radiation tube 27 according to a ratio corresponding to the temporary tomosynthesis imaging mAs value TB(i)_P which is the corrected irradiation condition for tomosynthesis imaging.

A process in a case in which the total mAs value is set and tomosynthesis imaging is performed without pre-imaging differs from the process in the flowchart illustrated in FIG. 24 in that Steps ST210 to ST250 are not performed, and a step of setting the total mAs value and a step of calculating the temporary tomosynthesis imaging mAs values TB(i)_P and calculating the sum of the temporary tomosynthesis imaging mAs values TB(i)_P are added. Therefore, the illustration and description of the process in the case in which the total mAs value is set and tomosynthesis imaging is performed without pre-imaging will not be repeated.

Second Embodiment

Figure 27:
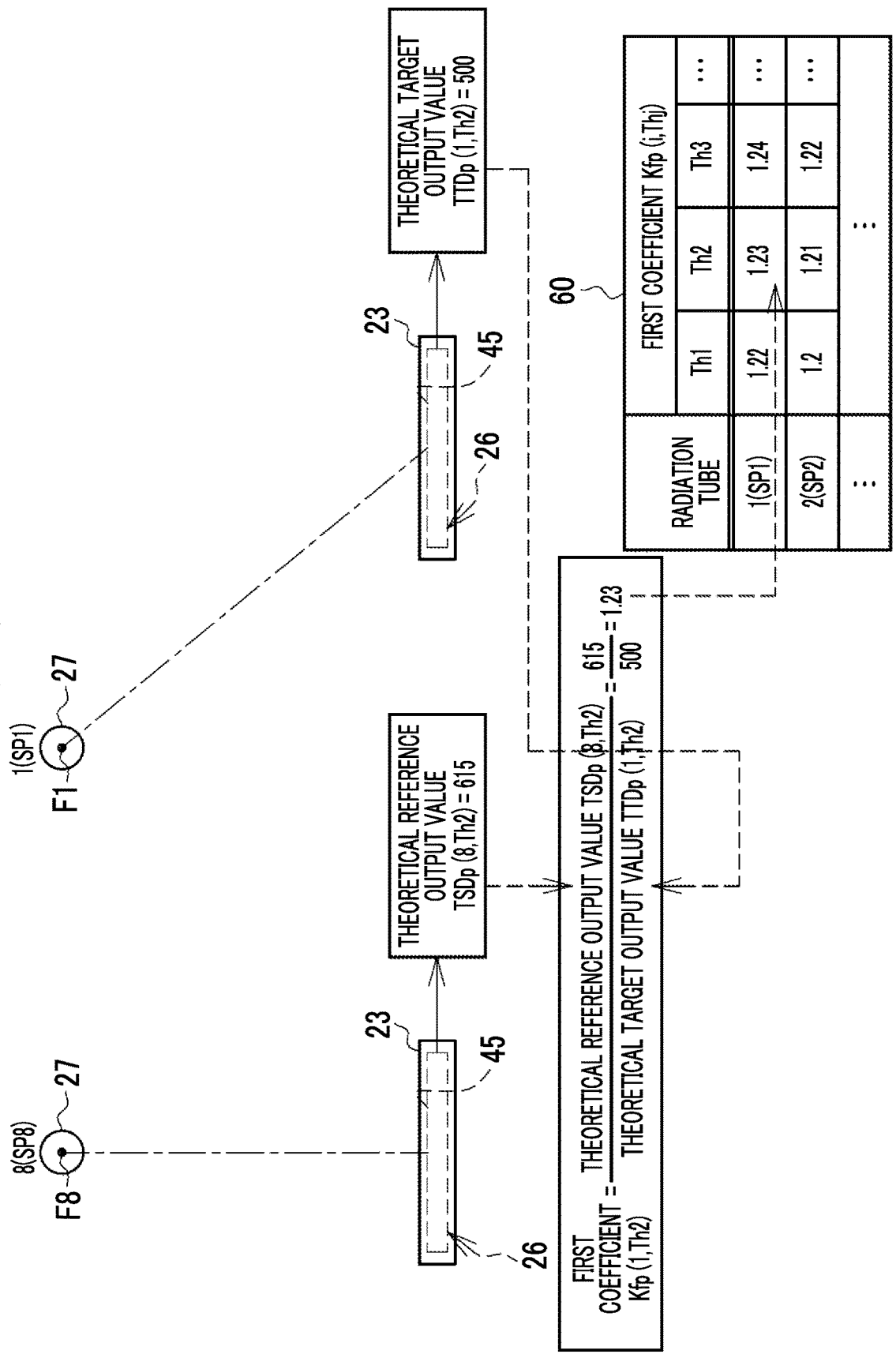
FIG. 27 is a diagram illustrating an aspect in which the first coefficient is calculated in a second embodiment.

A second embodiment illustrated in FIG. 27 differs from the first embodiment in a method for calculating the first coefficient Kfp(i, Thj). That is, in the first embodiment, the measured reference output value is divided by the measured target output value to calculate the first coefficient Kfp(i, Thj). In contrast, in the second embodiment, the first coefficient Kfp(i, Thj) is calculated using a theoretical reference output value and a theoretical target output value.

The theoretical reference output value is an output value that is theoretically estimated to be output from the radiation detector 26 receiving the radiation 37 emitted from the radiation tube 27 of which the irradiation angle is disposed at a reference position. In addition, the theoretical target output value is an output value that is theoretically estimated to be output from the radiation detector 26 receiving the radiation 37 emitted from the radiation tube 27 of which the first coefficient Kfp(i, Thj) is to be calculated.

A theoretical output value TDp(i, Thj) can be calculated by the following Expression (F):

$$TDp(i,Thj)=Df(i) \times 1^2 \div L(i)^2 \times \cos\theta(i) \times \exp\{-\mu \times Thj \div L\cos\theta(i)\} \quad (F).$$

In addition, Df(i) is the radiation dose of the radiation tube 27 with the number i, 1 is the distance from the radiation tube 27 to the measurement position of the radiation dose Df(i), L(i) is the distance from the radiation tube 27 with the number i to the center of the imaging surface 45 of the radiation detector 26, θ(i) is the irradiation angle of the radiation tube 27 with the number i, and μ is an absorption coefficient of the phantom 65 or the radiation 37. For example, Df(i) can be measured by the methods illustrated in FIGS. 17 to 19. In addition, 1 and L(i) can be measured by, for example, a measure. Further, θ(i) and μ are known values. Therefore, the theoretical output value TDp(i, Thj) can be obtained by simple calculation.

Here, the theoretical output value TDp(8, Thj) theoretically estimated to be output from the radiation detector 26 receiving the radiation 37 emitted from the radiation tube 27 disposed at the position SP8 where the irradiation angle is 0° is the theoretical reference output value TSDp. The position SP8 where the irradiation angle is 0° is an example of a "reference position" according to the technology of the present disclosure. Similarly to the first embodiment, the reference position is not limited to the position SP8 where the irradiation angle is 0°. The reference position may be a position in a predetermined irradiation angle range, for example, a position in an irradiation angle range of −10° to +10°.

The theoretical reference output value TSDp(8, Thj) is represented by the following Expression (E) obtained by substituting 0° into θ(i) of Expression (D):

$$TSDp(8,Thj)=Df(i) \times 12 \div L(i)^2 \times \exp(-\mu \times Thj) \quad (E).$$

The first coefficient Kfp(i, Thj) is calculated by dividing the theoretical reference output value TSDp(8, Thj) by the theoretical target output value TTDp(i, Thj).

FIG. 27 illustrates a case in which j is 2 and the radiation tube 27 of which the first coefficient Kfp(i, Thj) is to be calculated is the radiation tube 27 disposed at the position SP1 (i=1). In addition, FIG. 27 illustrates a case in which the theoretical reference output value TSDp(8, Th2) is 615 and the theoretical target output value TTDp(1, Th2) is 500. In this case, the first coefficient Kfp(1, Th1) is 615/500=1.23.

As such, in the second embodiment, the theoretical reference output value TSDp(i, Thj) theoretically estimated to be output from the radiation detector 26 receiving the radiation 37 emitted from the radiation tube 27 of which the irradiation angle is disposed at a reference position is divided by the theoretical target output value TTDp(i, Thj) theoretically estimated to be output from the radiation detector 26 receiving the radiation 37 emitted from the radiation tube 27, of which the first coefficient Kfp(i, Thj) is to be calculated, to calculate the first coefficient Kfp(i, Thj). Therefore, it is not necessary to analyze the actual output value of the radiation detector 26.

Third Embodiment

In a third embodiment illustrated in FIGS. 28 to 32, the second coefficient Kmd(i) is calibrated using the rate of reduction in the dose of radiation due to the deterioration of the radiation tube 27 over time.

Figure 28:
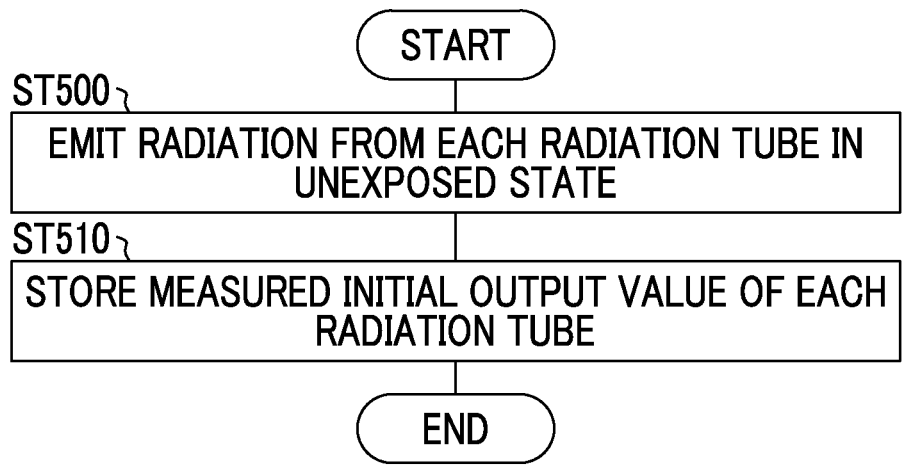
FIG. 28 is a flowchart illustrating the procedure of a process before a mammography apparatus is shipped in a third embodiment.
Figure 30:
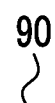
FIG. 30 is a diagram illustrating a measured initial output value table.

In the third embodiment, as illustrated in a flowchart of FIG. 28, first, before the mammography apparatus 10 is shipped, the radiation 37 is emitted from each radiation tube 27 in an unexposed state in which nothing is placed on the detector accommodation portion 23. (Step ST500). Then, the measured output value actually output from the radiation detector 26 receiving the radiation 37 emitted from each radiation tube 27 is stored as a measured initial output value in the storage device 55 (Step ST510). FIG. 30 illustrates a measured initial output value table 90 stored in the storage device 55.

Figure 29:
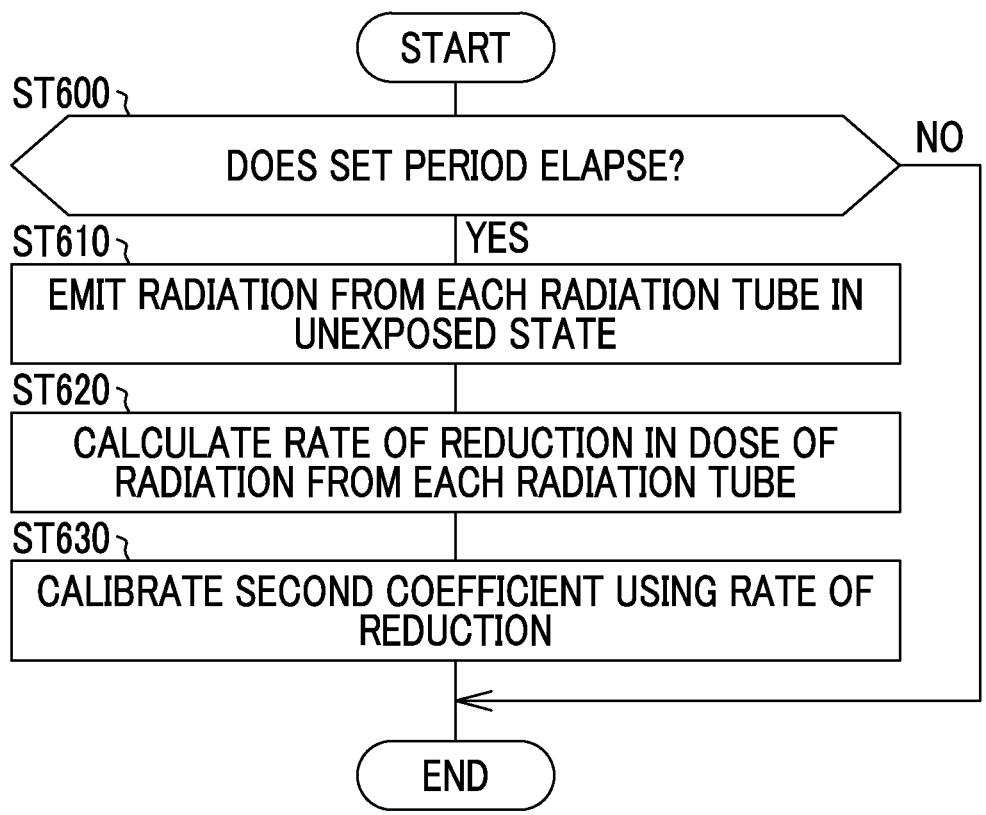
FIG. 29 is a flowchart illustrating the procedure of a process after the mammography apparatus is shipped in the third embodiment.

As illustrated in a flowchart of FIG. 29, in the mammography apparatus 10 after shipment, whenever a set period elapses (YES in Step ST600), the radiation 37 is emitted from each radiation tube 27 in the unexposed state, similarly to Step ST500 (Step ST610). The set period is, for example, half a year or one year.

Then, the rate of reduction in the dose of the radiation 37 from each radiation tube 27 is calculated on the basis of the measured initial output value stored in the storage device 55 in Step ST510 and a measured passage output value which is the measured output value actually output from the radiation detector 26 in Step ST610 (Step ST620). Specifically, as illustrated in FIG. 31, the measured passage output value is divided by the measured initial output value to calculate the rate of reduction.

As illustrated in Step ST630, the second coefficient Kmd (i) is calibrated using the calculated rate of reduction. Specifically, as illustrated in FIG. 32, a calibration unit 100 divides the second coefficient Kmd(i) of each radiation tube 27 by the rate of reduction to calibrate the second coefficient Kmd(i). The calibration unit 100 stores a calibrated second coefficient table 101 in which the calibrated second coefficient Kmd(i) has been registered in the storage device 55. The correction unit 52 corrects the irradiation condition using the second coefficient Kmd(i) registered in the calibrated second coefficient table 101.

As such, in the third embodiment, the calibration unit 100 calibrates the second coefficient Kmd(i) using the rate of reduction in the dose of radiation due to the deterioration of the radiation tube 27 over time. Therefore, it is possible to exclude the influence of deterioration over time from the second coefficient Kmd(i).

In some cases, the radiation tube 27 is newly replace. In this case, the first coefficient Kfp(i, Thj) in the first coefficient table 60 and the second coefficient Kmd(i) in the second coefficient table 61 are rewritten as a first coefficient Kfp(i, (Thj) and a second coefficient Kmd(i) of the newly replaced radiation tube 27, respectively.

In each of the above-described embodiments, the dosimeter 70 is used to calculate the second coefficient Kmd(i). However, the radiation detector 26 may be used as a substitute for the dosimeter 70. In this case, the output value from the radiation detector 26 is treated as the dose of radiation.

The first coefficient table 60 and the second coefficient table 61 may be stored in another apparatus connected to the control device 12. For example, the first coefficient tables 60 and the second coefficient tables 61 related to a plurality of apparatus main bodies 11 may be stored in a storage device of a management apparatus that collectively manages the plurality of apparatus main bodies 11. In this case, the acquisition unit 51 acquires the first coefficient Kfp(i, Thj) and the second coefficient Kmd(i) transmitted from the management apparatus.

Figure 33:
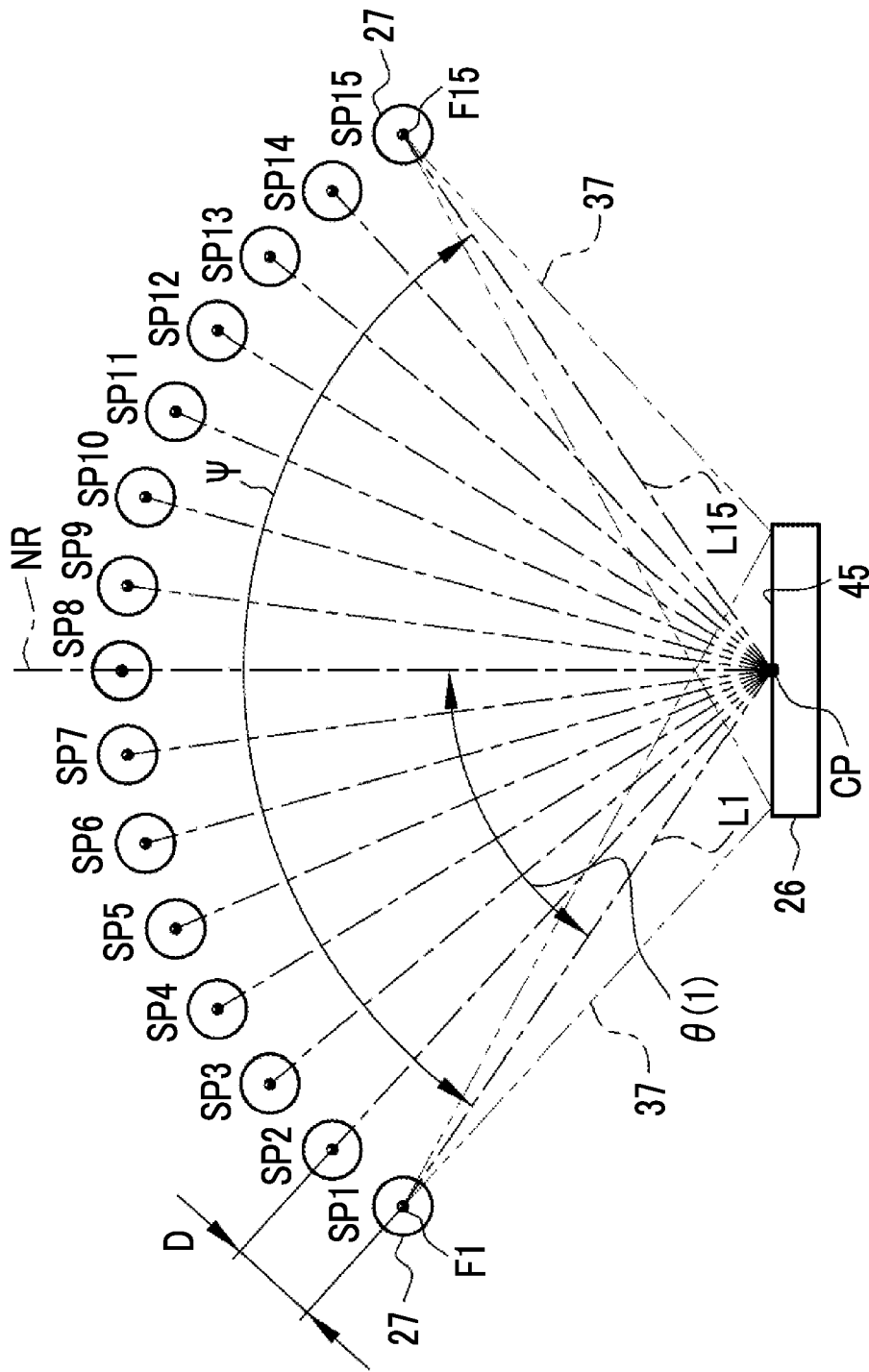
FIG. 33 is a diagram illustrating an example in which the radiation tubes are disposed at a plurality of positions where the focuses of radiation are arranged in an arc shape at equal intervals.

In each of the above-described embodiments, the positions where the focuses F are disposed are arranged in a linear shape. However, the present disclosure is not limited thereto. As illustrated in FIG. 33, the plurality of positions SP1 to SP15 where the focuses F1 to F15 are disposed may be arranged in an arc shape at equal intervals D. Even in a case in which the positions are arranged in the arc shape, the regularity of the arrangement positions SP1 to SP15 of the focuses F1 to F15 is ensured, similarly to the case in which the positions are arranged in the linear shape. Therefore, it is possible to simplify the process related to the generation of the tomographic image T.

Instead of the simple imaging in which the CC imaging illustrated in FIG. 6 and the MLO imaging illustrated in FIG. 7 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images obtained by the tomosynthesis imaging and a plurality of tomographic images T generated by the tomographic image generation unit 54.

In each of the above-described embodiments, the mammography apparatus 10 is given as an example of the tomosynthesis imaging apparatus. In the related art, performing tomosynthesis imaging in the mammography apparatus 10 has been found to be useful as a method for easily finding lesions such as microcalcifications of the breast M. Therefore, it is preferable to apply the tomosynthesis imaging apparatus according to the present disclosure to the mammography apparatus 10.

Of course, the tomosynthesis imaging apparatus according to the present disclosure may be applied to imaging apparatuses other than the mammography apparatus 10. For example, the tomosynthesis imaging apparatus according to the present disclosure may be applied to an imaging apparatus 150 illustrated in FIG. 34 which captures the image of the subject H during surgery.

The imaging apparatus 150 comprises an apparatus main body 151 having a control device (not illustrated) provided therein and an arm 152 having a substantially C-shape in a side view. A carriage 153 is attached to the apparatus main body 151 such that the apparatus main body 151 can be moved. The arm 152 includes a radiation source accommodation portion 154, a detector accommodation portion 155, and a main body portion 156. As in the mammography apparatus 10 illustrated in FIG. 1, the radiation source accommodation portion 154 accommodates a radiation source 157. In addition, the detector accommodation portion 155 accommodates a radiation detector 158. The radiation source accommodation portion 154 and the detector accommodation portion 155 are held by the main body portion 156 at a posture where they face each other.

The radiation source 157 and the radiation detector 158 have the same basic configurations as the radiation source 25 and the radiation detector 26 illustrated in FIG. 1, respectively. However, the imaging apparatus 150 captures an image of an object, such as the entire chest of the subject H, which is larger than the breast M. Therefore, a radiation tube 159 forming the radiation source 157 has a larger diameter than each radiation tube 27 of the mammography apparatus 10. In addition, the radiation detector 158 has an imaging surface 160 whose area is larger than that of the imaging surface 45 of the radiation detector 26. The number of radiation tubes 159 arranged may increase in order to respond to the capture of the image of a large object.

The detector accommodation portion 155 is inserted below a bed 161 on which the subject H lies supine. The bed 161 is made of a material that transmits the radiation 37. The radiation source accommodation portion 154 is provided above the subject H at a position that faces the detector accommodation portion 155 with the subject H interposed therebetween.

Similarly to the mammography apparatus 10, the imaging apparatus 150 performs correction using the first coefficient Kfp(i, Thj) such that the arrival dose is the same regardless of the irradiation angle. The imaging apparatus 150 can perform simple imaging using one radiation tube 159, in addition to the tomosynthesis imaging. In addition, instead of the simple imaging, the imaging apparatus 150 may generate a composite radiographic image. Further, the imaging apparatus 150 may capture both still radiographic images and moving radiographic images. Furthermore, reference numeral 162 indicates a housing for the radiation source 157.

The tomosynthesis imaging apparatus according to the present disclosure may be applied to a general radiography apparatus configured by combining a ceiling-suspended radiation source and an upright imaging table or a decubitus imaging table in which a radiation detector is set, in addition to the imaging apparatus 150 for surgery. Further, the tomosynthesis imaging apparatus according to the present disclosure may be applied to, for example, a cart-type mobile radiography apparatus which is moved to each hospital room and is used to capture the image of the subject H.

In the above-described embodiments, for example, the following various processors can be used as the hardware structure of processing units performing various processes, such as the control unit 50 (the pre-imaging control unit 50A and the tomosynthesis imaging control unit 50B), the acquisition unit 51, the correction unit 52, the setting unit 53, the tomographic image generation unit 54, and the calibration unit 100. The various processors include a CPU which is a general-purpose processor executing software to function as various processing units, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

It is possible to recognize the invention described in the following Supplementary Note 1 from the above description.

Supplementary Note 1

A tomosynthesis imaging apparatus comprises:
a radiation detector that detects radiation transmitted through an object and has an imaging surface capturing a projection image of the object; a radiation source having a plurality of radiation tubes disposed at a plurality of positions where the radiation is emitted to the imaging surface at different irradiation angles; an acquisition processor that acquires a first coefficient which corresponds to a thickness of the object, indicates a rate of change in an arrival dose of the radiation reaching the radiation detector depending on the irradiation angle, and is registered for each of the plurality of radiation tubes; a correction processor that corrects irradiation conditions of the radiation using the first coefficient; and a setting processor that sets the irradiation conditions corrected by the correction processor in the radiation source.

In the technology according to the present disclosure, the above-described various embodiments and various modifications may be appropriately combined with each other. The technology according to the present disclosure is not limited to each of the above-described embodiments and can adopt various configurations without departing from the scope and spirit of the present disclosure. In addition, the technology according to the present disclosure may be applied to a program and a storage medium that non-transitorily stores the program.

The contents described and illustrated above are the detailed description of portions related to the technology according to the present disclosure and are merely examples of the technology according to the present disclosure. For example, the description of the configurations, the functions, the operations, and the effects is the description of an example of the configurations, functions, operations, and effects of a portion according to the technology of the present disclosure. Therefore, for the contents described and illustrated above, unnecessary portions may be deleted or new elements may be added or replaced without departing from the scope and spirit of the technology according to the present disclosure. In the contents described and illustrated above, the description of common technical knowledge that does not require any explanation in order to enable the implementation of the technology according to the present disclosure is omitted in order to avoid complications and facilitate the understanding of the portions related to the technology according to the present disclosure.

All of the documents, the patent applications, and the technical standards described in the specification are incorporated by reference to the same extent as the incorporation of each of the documents, the patent applications and the technical standards by reference is specifically and individually stated.

What is claimed is:

1. A tomosynthesis imaging apparatus comprising:
a radiation detector that detects X-ray radiation transmitted through an object and has an imaging surface capturing a projection image of the object;
a radiation source having a plurality of radiation tubes disposed at a plurality of positions where the X-ray radiation is emitted to the imaging surface at different irradiation angles;
an acquisition unit that acquires a first coefficient which corresponds to a thickness of the object, indicates a rate of change in an arrival dose of the X-ray radiation reaching the radiation detector depending on the irradiation angle, and is registered for each of the plurality of radiation tubes;
a correction unit that corrects irradiation conditions of the X-ray radiation using the first coefficient; and
a setting unit that sets the irradiation conditions corrected by the correction unit in the radiation source,
wherein the acquisition unit acquires a second coefficient that is related to a dose of the X-ray radiation and is registered for each of the plurality of radiation tubes, and
wherein the correction unit corrects the irradiation conditions using the second coefficient in addition to the first coefficient.

2. The tomosynthesis imaging apparatus according to claim 1,
wherein the first coefficient is a value obtained by dividing a measured reference output value which has been actually output by the radiation detector receiving the X-ray radiation emitted from a radiation tube of which the irradiation angle is disposed at a reference position by a measured target output value which has been actually output by the radiation detector receiving the X-ray radiation emitted from a radiation tube of which the first coefficient is to be calculated.

3. The tomosynthesis imaging apparatus according to claim 1,
wherein the first coefficient is a value obtained by dividing a theoretical reference output value that is theoretically estimated to be output from the radiation detector receiving the X-ray radiation emitted from a radiation tube of which the irradiation angle is disposed at a reference position by a theoretical target output value that is theoretically estimated to be output from the radiation detector receiving the X-ray radiation emitted from a radiation tube of which the first coefficient is to be calculated.

4. The tomosynthesis imaging apparatus according to claim 1, further comprising:
a calibration unit that calibrates the second coefficient using a rate of reduction in the X-ray radiation dose caused by deterioration of the radiation tube over time.

5. The tomosynthesis imaging apparatus according to claim 1,
wherein the second coefficient is a tube current-irradiation time product per unit dose.

6. The tomosynthesis imaging apparatus according to claim 5,
wherein the correction unit corrects the tube current-irradiation time product included in the irradiation conditions.

7. The tomosynthesis imaging apparatus according to claim 1,
wherein, at the plurality of positions, focuses of the X-ray radiation are arranged in a linear shape or an arc shape at equal intervals.

8. The tomosynthesis imaging apparatus according to claim 1,
wherein the tomosynthesis imaging apparatus is a mammography apparatus that uses a breast as the object.

9. A method for operating a tomosynthesis imaging apparatus comprising a radiation detector that detects X-ray radiation transmitted through an object and has an imaging surface capturing a projection image of the object, the method comprising:
an acquisition step of acquiring, using a radiation source having a plurality of radiation tubes disposed at a plurality of positions where the X-ray radiation is emitted to the imaging surface at different irradiation angles, a first coefficient which corresponds to a thickness of the object, indicates a rate of change in an arrival dose of the X-ray radiation reaching the radiation detector depending on the irradiation angle, and is registered for each of the plurality of radiation tubes;
a correction step of correcting irradiation conditions of the X-ray radiation using the first coefficient; and
a setting step of setting the irradiation conditions corrected in the correction step in the radiation source,
wherein a second coefficient, that is related to a dose of the X-ray radiation and is registered for each of the plurality of radiation tubes, is acquired in the acquisition step, and
wherein the irradiation conditions are corrected by using the second coefficient in addition to the first coefficient in the correction step.

10. A non-transitory computer-readable storage medium storing a program for operating a tomosynthesis imaging apparatus comprising a radiation detector that detects X-ray radiation transmitted through an object and has an imaging surface capturing a projection image of the object and a radiation source having a plurality of radiation tubes disposed at a plurality of positions where the X-ray radiation is emitted to the imaging surface at different irradiation angles, the program causing a computer to function as:
an acquisition unit that acquires a first coefficient which corresponds to a thickness of the object, indicates a rate of change in an arrival dose of the X-ray radiation reaching the radiation detector depending on the irradiation angle, and is registered for each of the plurality of radiation tubes;
a correction unit that corrects irradiation conditions of the X-ray radiation using the first coefficient; and
a setting unit that sets the irradiation conditions corrected by the correction unit in the radiation source,
wherein the acquisition unit acquires a second coefficient that is related to a dose of the X-ray radiation and is registered for each of the plurality of radiation tubes, and
wherein the correction unit corrects the irradiation conditions using the second coefficient in addition to the first coefficient.

* * * * *